United States Patent
Hartwell et al.

(10) Patent No.: US 11,554,051 B2
(45) Date of Patent: Jan. 17, 2023

(54) NEGATIVE PRESSURE WOUND THERAPY APPARATUS

(71) Applicant: T.J. SMITH & NEPHEW, LIMITED, Watford (GB)

(72) Inventors: Edward Yerbury Hartwell, Hull (GB); Samuel John Mortimer, Kingston upon Hull (GB); Daniel Lee Steward, Kingston upon Hull (GB); Neill John Rawson, Doncaster (GB); Serena Louisa Russell, York (GB)

(73) Assignee: T.J. Smith and Nephew, Limited, Hull (GB)

(*) Notice: Subject to any disclaimer, the term of this patent is extended or adjusted under 35 U.S.C. 154(b) by 0 days.

(21) Appl. No.: 16/624,762

(22) PCT Filed: Jun. 21, 2018

(86) PCT No.: PCT/EP2018/066570
§ 371 (c)(1),
(2) Date: Dec. 19, 2019

(87) PCT Pub. No.: WO2019/002085
PCT Pub. Date: Jan. 3, 2019

(65) Prior Publication Data
US 2021/0137743 A1    May 13, 2021

Related U.S. Application Data

(60) Provisional application No. 62/528,914, filed on Jul. 5, 2017, provisional application No. 62/528,893, filed (Continued)

(51) Int. Cl.
*A61F 13/00* (2006.01)
*A61F 13/02* (2006.01)
*A61M 1/00* (2006.01)

(52) U.S. Cl.
CPC ...... *A61F 13/00068* (2013.01); *A61F 13/022* (2013.01); *A61F 13/0216* (2013.01); *A61M 1/90* (2021.05); *A61M 1/91* (2021.05)

(58) Field of Classification Search
CPC ............ A61F 13/00068; A61F 13/0216; A61F 13/022; A61M 1/90; A61M 1/91
(Continued)

(56) References Cited

U.S. PATENT DOCUMENTS 2,331,271 A    10/1943    Gilchrist
2,727,382 A    12/1955    Karl et al.
(Continued)

FOREIGN PATENT DOCUMENTS

CN    1293953 A    5/2001
CN    2676918 Y    2/2005
(Continued)

OTHER PUBLICATIONS

Invitation to Pay Additional Fees and Partial Search Report, re PCT Application No. PCT/EP2018/066570, dated Sep. 7, 2018.
(Continued)

*Primary Examiner* — Nicholas J. Weiss
*Assistant Examiner* — Seth Han
(74) *Attorney, Agent, or Firm* — Knobbe, Martens, Olson & Bear, LLP

(57) ABSTRACT

Disclosed embodiments relate to apparatuses and methods for wound treatment. In certain embodiments, a negative pressure wound therapy apparatus can include a wound dressing comprising an absorbent layer comprising a plurality of portions of absorbent material that can be physically separate from each other. In some embodiments, a wound treatment apparatus can include an absorbent layer comprising a compressed portion configured to impede the flow of fluid therethrough. In some embodiments, a wound treat-
(Continued)

ment apparatus can include an absorbent layer and spacer layer positioned side by side.

15 Claims, 36 Drawing Sheets

Related U.S. Application Data on Jul. 5, 2017, provisional application No. 62/527,457, filed on Jun. 30, 2017.

(58) Field of Classification Search
USPC .......................................................... 604/313
See application file for complete search history.

(56) References Cited

U.S. PATENT DOCUMENTS

| | | | |
|---|---|---|---|
| 2,877,765 A | 3/1959 | John et al. |
| 2,889,039 A | 6/1959 | Peter et al. |
| 3,073,304 A | 1/1963 | Schaar |
| 3,285,245 A | 11/1966 | Eldredge et al. |
| 3,964,039 A | 6/1976 | Craford et al. |
| 4,093,277 A | 6/1978 | Nolan et al. |
| 4,095,599 A | 6/1978 | Simonet-Haibe |
| 4,224,941 A | 9/1980 | Stivala |
| 4,541,426 A | 9/1985 | Webster |
| 4,624,656 A | 11/1986 | Clark et al. |
| 4,681,562 A | 7/1987 | Beck et al. |
| 4,690,134 A | 9/1987 | Snyders |
| 4,699,134 A | 10/1987 | Samuelsen |
| 4,770,187 A | 9/1988 | Lash et al. |
| 4,886,697 A | 12/1989 | Perdelwitz, Jr. et al. |
| 4,985,467 A | 1/1991 | Kelly et al. |
| 5,000,172 A | 3/1991 | Ward |
| 5,000,741 A | 3/1991 | Kalt |
| 5,080,661 A | 1/1992 | Lavender et al. |
| 5,152,757 A | 10/1992 | Eriksson |
| 5,264,218 A | 11/1993 | Rogozinski |
| 5,267,952 A | 12/1993 | Gardner |
| 5,360,420 A | 11/1994 | Cook et al. |
| 5,536,555 A | 7/1996 | Zelazoski et al. |
| 5,549,584 A | 8/1996 | Gross |
| 5,562,107 A | 10/1996 | Lavender et al. |
| 5,591,149 A | 1/1997 | Cree et al. |
| 5,626,954 A | 5/1997 | Andersen et al. |
| 5,643,189 A | 7/1997 | Masini |
| 5,795,439 A | 8/1998 | Euripides et al. |
| 5,795,584 A | 8/1998 | Totakura et al. |
| 5,804,021 A | 9/1998 | Abuto et al. |
| 5,833,646 A | 11/1998 | Masini |
| 5,868,724 A | 2/1999 | Diercks, Jr. et al. |
| 5,968,855 A | 10/1999 | Perdelwitz, Jr. et al. |
| 6,018,092 A | 1/2000 | Dunshee |
| 6,071,267 A | 6/2000 | Zamierowski |
| 6,142,982 A | 11/2000 | Hunt et al. |
| 6,207,875 B1 | 3/2001 | Lindqvist et al. |
| 6,225,523 B1 | 5/2001 | Masini |
| 6,241,697 B1 | 6/2001 | Augustine |
| 6,261,283 B1 | 7/2001 | Morgan et al. |
| 6,297,422 B1 | 10/2001 | Hansen et al. |
| 6,345,623 B1 | 2/2002 | Heaton et al. |
| 6,398,767 B1 | 6/2002 | Fleischmann |
| 6,447,799 B1 | 9/2002 | Ullman |
| 6,478,781 B1 | 11/2002 | Urich et al. |
| 6,482,491 B1 | 11/2002 | Samuelsen et al. |
| 6,497,688 B2 | 12/2002 | Lasko |
| 6,566,575 B1 | 5/2003 | Stickels et al. |
| 6,599,262 B1 | 7/2003 | Masini |
| 6,685,681 B2 | 2/2004 | Lockwood et al. |
| 6,764,462 B2 | 7/2004 | Risk, Jr. et al. |
| 6,767,334 B1 | 7/2004 | Randolph |
| 6,951,553 B2 | 10/2005 | Bubb et al. |
| 6,979,324 B2 | 12/2005 | Bybordi et al. |
| 6,998,511 B2 | 2/2006 | Worthley |
| 7,004,915 B2 | 2/2006 | Boynton et al. |
| 7,022,113 B2 | 4/2006 | Lockwood et al. |
| D525,362 S | 7/2006 | Nielsen et al. |
| 7,070,584 B2 | 7/2006 | Johnson et al. |
| 7,108,683 B2 | 9/2006 | Zamierowski |
| D537,948 S | 3/2007 | Smith |
| 7,198,046 B1 | 4/2007 | Argenta et al. |
| 7,267,681 B2 | 9/2007 | Dunshee |
| 7,381,859 B2 | 6/2008 | Hunt et al. |
| 7,429,689 B2 | 9/2008 | Chen et al. |
| 7,468,471 B2 | 12/2008 | Sigurjonsson et al. |
| 7,534,927 B2 | 5/2009 | Lockwood et al. |
| 7,553,306 B1 | 6/2009 | Hunt et al. |
| 7,576,256 B2 | 8/2009 | Bjornberg et al. |
| 7,625,362 B2 | 12/2009 | Boehringer et al. |
| 7,674,948 B2 | 3/2010 | Propp et al. |
| 7,678,102 B1 | 3/2010 | Heaton |
| 7,753,894 B2 | 7/2010 | Blott et al. |
| 7,759,537 B2 | 7/2010 | Bishop et al. |
| 7,812,212 B2 | 10/2010 | Propp et al. |
| 7,976,519 B2 | 7/2011 | Bubb et al. |
| 7,982,087 B2 | 7/2011 | Greener et al. |
| 8,021,347 B2 | 9/2011 | Vitaris et al. |
| 8,034,037 B2 | 10/2011 | Adams et al. |
| 8,404,921 B2 | 3/2013 | Lee et al. |
| 8,540,687 B2 | 9/2013 | Henley et al. |
| 8,680,360 B2 | 3/2014 | Greener et al. |
| 8,764,732 B2 | 7/2014 | Hartwell |
| 8,791,316 B2 | 7/2014 | Greener |
| 8,801,685 B2 | 8/2014 | Armstrong et al. |
| D712,546 S | 9/2014 | Igwebuike et al. |
| D785,189 S | 4/2017 | Dettmar |
| 9,770,368 B2 | 9/2017 | Robinson et al. |
| 9,820,888 B2 | 11/2017 | Greener et al. |
| RE47,100 E | 10/2018 | Smith et al. |
| D870,719 S | 12/2019 | Peters et al. |
| 10,548,776 B2 | 2/2020 | Greener et al. |
| 10,555,839 B2 | 2/2020 | Hartwell |
| 10,695,226 B2 | 6/2020 | Collinson et al. |
| 10,765,561 B2 | 9/2020 | Lattimore et al. |
| 11,298,454 B2 | 4/2022 | Weston |
| 2001/0034499 A1 | 10/2001 | Sessions et al. |
| 2001/0051165 A1 | 12/2001 | Lenz et al. |
| 2002/0035352 A1 | 3/2002 | Ronnberg et al. |
| 2002/0052570 A1 | 5/2002 | Naimer |
| 2002/0082567 A1 | 6/2002 | Lockwood et al. |
| 2002/0183702 A1 | 12/2002 | Henley et al. |
| 2003/0014025 A1 | 1/2003 | Allen et al. |
| 2003/0014786 P1 | 1/2003 | Meilland |
| 2003/0108587 A1 | 6/2003 | Orgill et al. |
| 2003/0212357 A1 | 11/2003 | Pace |
| 2004/0019338 A1 | 1/2004 | Litvay et al. |
| 2004/0064132 A1 | 4/2004 | Boehringer et al. |
| 2004/0087884 A1 | 5/2004 | Haddock et al. |
| 2004/0167482 A1 | 8/2004 | Watson |
| 2005/0084641 A1 | 4/2005 | Downs et al. |
| 2005/0090860 A1 | 4/2005 | Paprocki |
| 2006/0020234 A1 | 1/2006 | Chou et al. |
| 2006/0047257 A1 | 3/2006 | Raidel et al. |
| 2006/0155260 A1 | 7/2006 | Blott et al. |
| 2006/0184150 A1 | 8/2006 | Noel |
| 2007/0032763 A1 | 2/2007 | Vogel |
| 2007/0060892 A1 | 3/2007 | Propp |
| 2007/0073200 A1 | 3/2007 | Hannigan et al. |
| 2007/0220692 A1 | 9/2007 | Kusin |
| 2007/0239232 A1 | 10/2007 | Kurtz et al. |
| 2007/0265586 A1 | 11/2007 | Joshi et al. |
| 2008/0113143 A1* | 5/2008 | Taylor ................ B32B 5/18 428/47 |
| 2008/0172017 A1 | 7/2008 | Carlucci et al. |
| 2009/0012483 A1 | 1/2009 | Blott et al. |
| 2009/0043268 A1 | 2/2009 | Eddy et al. |
| 2009/0099519 A1 | 4/2009 | Kaplan |
| 2009/0105670 A1 | 4/2009 | Bentley et al. |
| 2009/0227968 A1 | 9/2009 | Vess |
| 2009/0227969 A1* | 9/2009 | Jaeb ................ A61F 13/00068 604/313 |
| 2009/0234309 A1 | 9/2009 | Vitaris et al. |
| 2009/0240185 A1 | 9/2009 | Jaeb et al. |
| 2009/0306609 A1 | 12/2009 | Blott et al. |

(56) References Cited

U.S. PATENT DOCUMENTS

| | | |
|---|---|---|
| 2009/0326430 A1 | 12/2009 | Frederiksen et al. |
| 2010/0063484 A1 | 3/2010 | Heagle |
| 2010/0069858 A1 | 3/2010 | Olson |
| 2010/0087767 A1 | 4/2010 | McNeil |
| 2010/0106113 A1 | 4/2010 | Heinecke |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0174250 A1 | 7/2010 | Hu et al. |
| 2010/0198127 A1 | 8/2010 | Addison |
| 2010/0305526 A1 | 12/2010 | Robinson et al. |
| 2010/0312159 A1 | 12/2010 | Aali et al. |
| 2010/0318043 A1 | 12/2010 | Malhi et al. |
| 2011/0004172 A1 | 1/2011 | Eckstein et al. |
| 2011/0021964 A1 | 1/2011 | Larsen et al. |
| 2011/0034892 A1 | 2/2011 | Buan |
| 2011/0054421 A1 | 3/2011 | Hartwell |
| 2011/0070391 A1 | 3/2011 | Cotton |
| 2011/0077605 A1 | 3/2011 | Karpowicz et al. |
| 2011/0092927 A1 | 4/2011 | Wilkes et al. |
| 2011/0112492 A1 | 5/2011 | Bharti et al. |
| 2011/0184364 A1 | 7/2011 | Biggs et al. |
| 2011/0230849 A1 | 9/2011 | Coulthard et al. |
| 2011/0282309 A1* | 11/2011 | Adie .............. A61F 13/0209 604/319 |
| 2011/0313373 A1 | 12/2011 | Riesinger |
| 2011/0313374 A1 | 12/2011 | Lockwood et al. |
| 2011/0319801 A1 | 12/2011 | Ital et al. |
| 2012/0041402 A1 | 2/2012 | Greener |
| 2012/0095380 A1 | 4/2012 | Gergely et al. |
| 2012/0136326 A1 | 5/2012 | Croizat et al. |
| 2012/0209226 A1 | 8/2012 | Simmons et al. |
| 2012/0220973 A1 | 8/2012 | Chan et al. |
| 2012/0308780 A1 | 12/2012 | Rottger et al. |
| 2013/0211349 A1 | 8/2013 | Stokes et al. |
| 2015/0190286 A1* | 7/2015 | Allen .............. A61F 13/00017 604/319 |
| 2016/0022500 A1 | 1/2016 | Tumey |
| 2016/0144084 A1* | 5/2016 | Collinson ......... A61F 13/00068 604/319 |
| 2017/0007751 A1 | 1/2017 | Hartwell et al. |
| 2018/0185558 A1 | 7/2018 | Weston |
| 2018/0361039 A1 | 12/2018 | Greener |
| 2019/0008690 A1 | 1/2019 | Adie et al. |
| 2019/0008696 A1 | 1/2019 | Allen et al. |
| 2019/0091381 A1 | 3/2019 | Askem et al. |
| 2019/0142647 A1 | 5/2019 | Hartwell |
| 2019/0231600 A1 | 8/2019 | Locke et al. |
| 2020/0155356 A1 | 5/2020 | Greener et al. |
| 2020/0383838 A1 | 12/2020 | Locke et al. |
| 2021/0007897 A1 | 1/2021 | Greener et al. |

FOREIGN PATENT DOCUMENTS

| | | |
|---|---|---|
| CN | 2843399 Y | 12/2006 |
| CN | 201139694 Y | 10/2008 |
| CN | 101415818 A | 4/2009 |
| CN | 201375590 Y | 1/2010 |
| CN | 201418816 Y | 3/2010 |
| CN | 102089017 A | 6/2011 |
| CN | 102274574 A | 12/2011 |
| CN | 102458334 A | 5/2012 |
| CN | 202263100 U | 6/2012 |
| DE | 4030465 A1 | 4/1992 |
| EP | 0768071 A1 | 4/1997 |
| EP | 1353001 A1 | 10/2003 |
| EP | 0630629 B1 | 11/2004 |
| EP | 2269603 B1 | 5/2015 |
| EP | 2538902 B1 | 9/2015 |
| FR | 1163907 A | 10/1958 |
| GB | 2331937 A | 6/1999 |
| GB | 2389794 A | 12/2003 |
| JP | S5230463 U | 3/1977 |
| JP | S57119738 A | 7/1982 |
| JP | H02131432 U | 11/1990 |
| JP | H0788131 A | 4/1995 |
| JP | H07231909 A | 9/1995 |
| JP | 2006025918 A | 2/2006 |
| JP | 2008073187 A | 4/2008 |
| JP | 2008183244 A | 8/2008 |
| JP | 2011521736 A | 7/2011 |
| JP | 2011530344 A | 12/2011 |
| JP | 2012016476 A | 1/2012 |
| JP | 6307504 B2 | 4/2018 |
| RU | 62504 U1 | 4/2007 |
| RU | 2432177 C1 | 10/2011 |
| WO | WO-9741816 A1 | 11/1997 |
| WO | WO-9963922 A1 | 12/1999 |
| WO | WO-0154743 A1 | 8/2001 |
| WO | WO-03051409 A1 | 6/2003 |
| WO | WO-03086232 A2 | 10/2003 |
| WO | WO-2005009488 A2 | 2/2005 |
| WO | WO-2006087021 A1 | 8/2006 |
| WO | WO-2007066699 A1 | 6/2007 |
| WO | WO-2008100437 A1 | 8/2008 |
| WO | WO-2009001590 A1 | 12/2008 |
| WO | WO-2009021523 A1 | 2/2009 |
| WO | WO-2009111657 A2 | 9/2009 |
| WO | WO-2009114760 A1 | 9/2009 |
| WO | WO-2009135171 A2 | 11/2009 |
| WO | WO-2009156949 A2 | 12/2009 |
| WO | WO-2010010398 A1 | 1/2010 |
| WO | WO-2010016791 A1 | 2/2010 |
| WO | WO-2010122665 A1 | 10/2010 |
| WO | WO-2011028407 A1 | 3/2011 |
| WO | WO-2011040970 A1 * | 4/2011 ........... B29C 70/086 |
| WO | WO-2011087871 A2 | 7/2011 |
| WO | WO-2011112870 A1 | 9/2011 |
| WO | WO-2011130551 A1 | 10/2011 |
| WO | WO-2011135284 A1 | 11/2011 |
| WO | WO-2011135286 A1 | 11/2011 |
| WO | WO-2011144888 A1 | 11/2011 |
| WO | WO-2011152368 A1 | 12/2011 |
| WO | WO-2012087376 A1 | 6/2012 |
| WO | WO-2013007973 A2 | 1/2013 |
| WO | WO-2013175306 A2 | 11/2013 |
| WO | WO-2014020400 A2 | 2/2014 |
| WO | WO-2014020440 A1 | 2/2014 |
| WO | WO-2017133376 A1 | 8/2017 |
| WO | WO 2019/002085 | 1/2019 |

OTHER PUBLICATIONS

International Search Report and Written Opinion, re PCT Application No. PCT/EP2018/066570, dated Nov. 14, 2018.
International Preliminary Reporton Patentability for Application No. PCT/EP2018/066570, dated Jan. 9, 2020, 10 pages
KCI Licensing Inc, "Prevena™ Incision Management System—Clinician Guide—Instructions for Use," 390061 Rev D, Jan. 2010, 10 pages.
KCI Licensing Inc, "Prevena™ Incision Management System—Clinician Guide—Instructions for Use," 390153-WEB Rev B, Jan. 2010, 12 pages.
KCI Licensing, "PREVENA™ Incision Management System—Patient Guide", 390064 Rev D, Jan. 2010, 4 pages.
KCI Licensing, "PREVENA™ Incision Management System—Patient Guide," 390152-WEB C, Jan. 2011, 6 pages.
KCI Licensing, Prevena™ Incision Management System, Jun. 22, 2010, in 2 pages.
Smith & Nephew, Allevyn Gentle Border Multisite, Jun. 2011, 2 pages.
Smith and Nephew Inc., "Allevyn Wound Dressings Pamphlet," 2008, 2 pages.
Smith and Nephew Medical Ltd., "Reach for the Right Dressing. Reach for ALLEVYN," Allevyn Educational Booklet, Apr. 2014, 2 pages.
U.S. Appl. No. 16/132,115, Wound Dressing and Method of Treatment, filed Sep. 14, 2018.
Declaration of Nadeem Bridi submitted in the Opposition against EP2395957, dated Jan. 25, 2017, 1 page.

(56) References Cited

OTHER PUBLICATIONS

Emerging Technologies, "Chem-Posite™ 11C-450," Technical Data, the superabsorbent source (publication date unknown), 1 page.
KCI, Inc., "V.A.C. Therapy Safety Information," leaflet, 2008, 4 pages.
U.S. Appl. No. 12/886,088, Systems and Methods for Using Negative Pressure Wound Therapy to Manage Open Abdominal Wounds, filed Sep. 20, 2010.
U.S. Appl. No. 14/333,125, Systems and Methods for Using Negative Pressure Wound Therapy to Manage Open Abdominal Wounds, filed Jul. 16, 2014.
U.S. Appl. No. 17/009,523, Systems and Methods for Using Negative Pressure Wound Therapy to Manage Open Abdominal Wounds, filed Sep. 1, 2020.
U.S. Appl. No. 17/743,371, Wound Dressing and Method of Treatment, filed May 12, 2022.
U.S. Appl. No. 17/461,756, Wound Dressing, filed Aug. 30, 2021.
U.S. Appl. No. 15/872,880, Reduced Pressure Treatment System, filed Jan. 16, 2018.

* cited by examiner

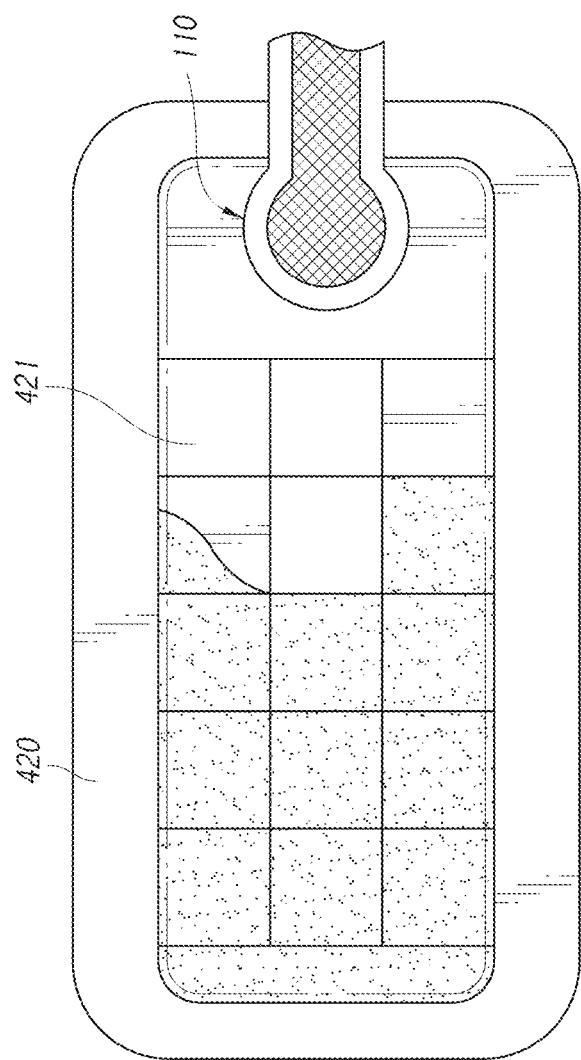

NEGATIVE PRESSURE WOUND THERAPY APPARATUS

CROSS-REFERENCE TO RELATED APPLICATIONS

This application is a U.S. national stage application of International Patent Application No. PCT/EP2018/066570, filed Jun. 21, 2018, which claims priority to U.S. Provisional Patent Application No. 62/527,457, filed on Jun. 30, 2017, U.S. Provisional Patent Application No. 62/528,914, filed on Jul. 5, 2017 and U.S. Provisional Patent Application No. 62/528,893, filed on Jul. 5, 2017, which are hereby incorporated by reference in their entirety and made part of this disclosure.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Wound dressings for use in negative pressure can have a lifetime of the wound dressing associated with the liquid absorbency capacity of the dressing. The shortened lifetime can be observed due to problems of the fluid pathway to the port being blocked before the dressing is at full absorbent capacity. It may be desirable, in some situations, to provide a fluid flow pathway that prevents or decreases the blocking of the port until the full lifetime of the dressing is achieved.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein.

In some embodiments, a wound treatment apparatus can comprise a wound dressing configured to be positioned over a wound site. The wound dressing can comprise an absorbent layer for absorbing wound exudate, the absorbent layer comprising at least a first portion of absorbent material and a second portion of absorbent material physically separate from the first portion and adjacent to the first portion in the same plane, a backing layer over the absorbent layer and comprising at least one orifice, and a fluidic connector positioned over the at least one orifice configured to provide negative pressure through the wound dressing to the wound site.

The apparatus of the preceding paragraph may also include any combination of the features described in the following paragraphs, among others described herein. Each of the features described in the following paragraphs may also be part of another embodiment that does not necessarily include all of the features of the previous paragraph.

The first portion of absorbent material can be separated from the second portion of absorbent material by a space.

The absorbent layer can comprise a 1-10 mm gap separating each physically separate portion of absorbent material.

The backing layer can extend at least partially into the space.

The backing layer can comprise folds configured to extend into the space between the first and second portions of the absorbent material.

The backing layer can be vacuum formed over the absorbent layer to thereby fill the space between the first and second portions of the absorbent material.

The wound treatment apparatus can further comprise a first transmission layer beneath the absorbent layer.

The backing layer can contact the transmission layer in a space between the first and second portions of absorbent material.

The first portion can be larger than the second portion.

The absorbent layer can further comprise a plurality of second portions, wherein each of the plurality of second portions is physically separate from each other second portion and the first portion.

The absorbent layer can comprise a plurality of physically separate portions each having a shape selected from the group consisting of a square, rectangle, circle, pentagon, hexagon, octagon, and triangle.

The absorbent layer can comprise a plurality of physically separate portions having a rectangular shape.

The absorbent layer can comprise a plurality of portions all of which have the same shape and size.

The absorbent layer can comprise a plurality of portions having different shapes and sizes.

The absorbent layer can comprise a plurality of portions arranged in a regularly repeating grid pattern.

The first portion of absorbent material can be positioned below the orifice in the backing layer.

The wound treatment apparatus can further comprise a wound contact layer beneath the absorbent layer and sealed to the backing layer.

The wound treatment apparatus can further comprise a source of negative pressure configured to be in fluid communication with a wound site through the wound dressing.

The wound dressing apparatus can further comprise a second transmission layer above the absorbent layer.

The fluidic connector can comprise a filter.

In some embodiments, a wound treatment apparatus for treatment of a wound site is provided. The wound treatment apparatus comprises a wound dressing configured to be positioned over a wound site. The wound dressing comprises an absorbent layer for absorbing wound exudate, the absorbent layer comprising at least one compressed portion configured to impede the flow of fluid therethrough. The wound dressing also comprises a backing layer over the absorbent layer.

The apparatus of the preceding paragraph may also include any combination of the features described in the following paragraphs, among others described herein. Each of the features described in the following paragraphs may also be part of another embodiment that does not necessarily include all of the features of the previous paragraph.

The compressed portion may impede the flow of fluid between portions of the absorbent layer adjacent to the compressed portion.

The compressed portion may block the flow of fluid therethrough.

The compressed portion may block the flow of fluid between portions of the absorbent layer adjacent to the compressed portion.

The absorbent layer may have a length and a width, the compressed portion extending across the entire width of the absorbent layer.

The wound treatment apparatus may comprise at least a first compressed portion and a second compressed portion configured to impede the flow of fluid therethrough.

The absorbent layer has a length and a width, the first compressed portion and the second compressed portion each extending across the entire width of the absorbent layer.

The absorbent layer may comprise a vertical hole positioned below the opening in the backing layer.

The compressed portion may surround the vertical hole in absorbent layer.

The absorbent layer may comprise a superabsorbent material.

The absorbent layer may comprise a non-woven material.

The absorbent layer may comprise foam.

The compressed portion may be formed by calendering the absorbent material.

The backing layer may comprise at least one orifice.

The wound treatment apparatus may further comprise a fluidic connector positioned over the orifice in the backing layer.

The wound treatment apparatus may further comprise a wound contact layer beneath the absorbent layer and sealed to the backing layer.

The wound treatment apparatus may further comprise a source of negative pressure configured to be in fluid communication with a wound site through the wound dressing.

In some embodiments, a wound treatment apparatus for treatment of a wound site, can comprise a wound dressing configured to be positioned over a wound site. The wound dressing can comprise a spacer layer, an absorbent layer for absorbing wound exudate, the absorbent layer and spacer layer positioned side by side, a backing layer over the absorbent layer and the spacer layer and comprising at least one orifice positioned over the absorbent layer, and a fluidic connector positioned over the at least one orifice configured to provide negative pressure through the wound dressing to the wound site.

The apparatus of the preceding paragraph may also include any combination of the features described in the following paragraphs, among others described herein. Each of the features described in the following paragraphs may also be part of another embodiment that does not necessarily include all of the features of the previous paragraph.

The spacer layer can distribute negative pressure to the wound.

The spacer layer can be in contact with the backing layer and the backing layer is configured to allow liquid from wound exudates to be transferred through the backing layer and evaporated from an outer surface of the backing layer.

The absorbent layer can surround the outer perimeter of the spacer layer.

The absorbent layer can be configured to provide leak protection around the outside of the spacer.

The absorbent layer can comprise a vertical hole positioned below the orifice in the backing layer.

The absorbent layer can comprise a superabsorbent material.

The absorbent layer can comprise a non-woven material.

The absorbent layer can comprise foam.

The wound treatment apparatus can further comprise a wound contact layer beneath the absorbent layer and spacer layer and sealed to the backing layer.

The absorbent layer and spacer layer are the only layers positioned between the wound contact layer and the cover layer.

The wound treatment apparatus can further comprise one or more additional spacer layers positioned below the side by side absorbent and spacer layer.

The wound treatment apparatus can further comprise one or more additional spacer layers positioned above the side by side absorbent and spacer layer.

The wound treatment apparatus can further comprise one or more additional absorbent layers positioned below the side by side absorbent and spacer layer.

The wound treatment apparatus can further comprise one or more additional absorbent layers positioned above the side by side absorbent and spacer layer.

The wound treatment apparatus can further comprise a source of negative pressure configured to be in fluid communication with a wound site through the wound dressing.

The fluidic connector can be positioned over the absorbent layer, and the spacer layer is positioned next to the absorbent layer away from the fluidic connector.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 4D-4F illustrate embodiments of a wound dressing with an absorbent layer formed from physically separated portions and/or units of absorbent material for use within a negative pressure wound treatment system;

DETAILED DESCRIPTION

Figure 1A:
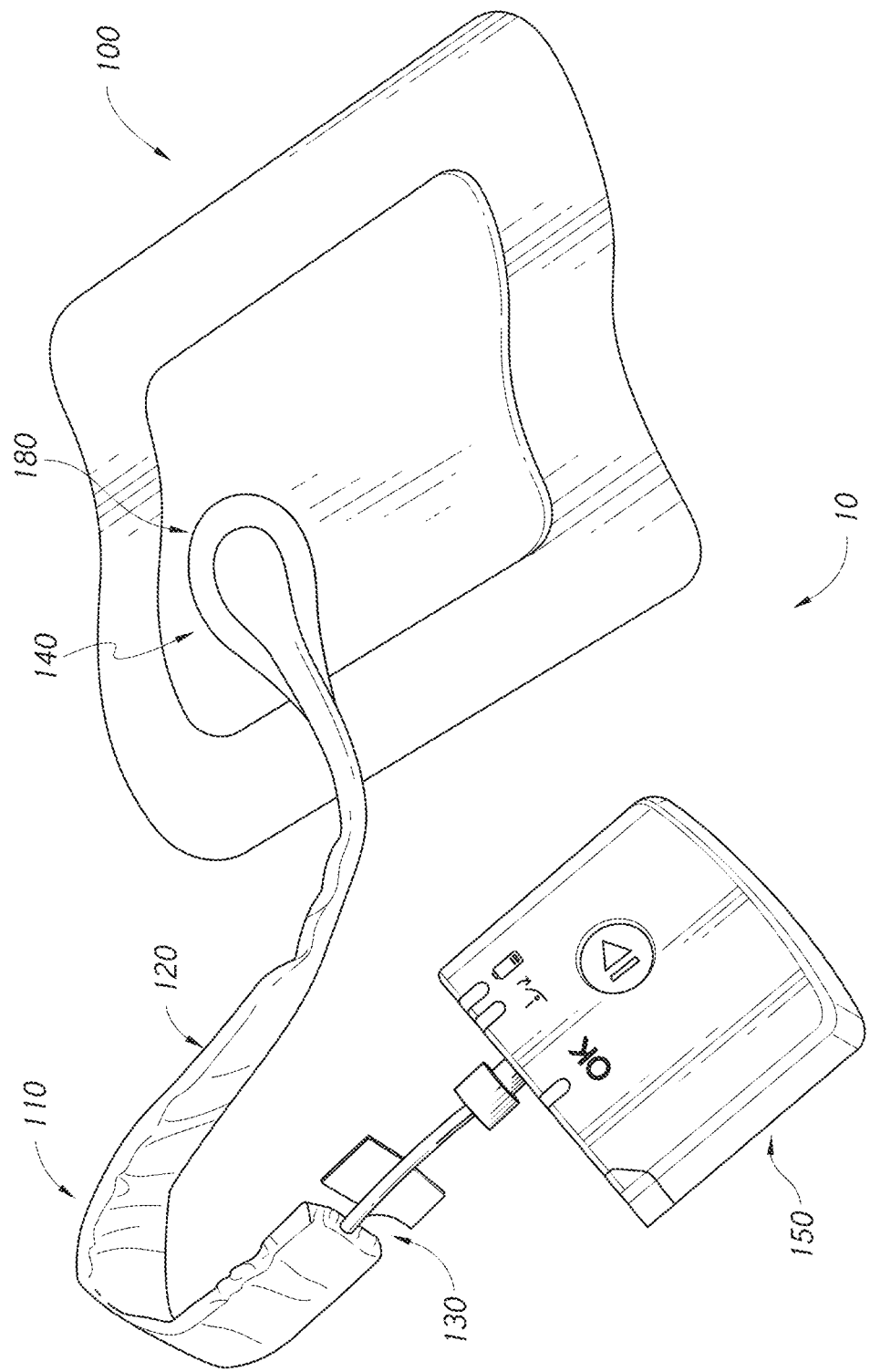
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found in U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,874, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as US2011/0282309, titled "WOUND DRESSING AND METHOD OF USE," and U.S. patent application Ser. No. 14/715,527, filed May 18, 2015, published as US2016/0339158, titled "FLUIDIC CONNECTOR FOR NEGATIVE PRESSURE WOUND THERAPY," the disclosures of which are hereby incorporated by reference in their entireties, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in International Application No. PCT/EP2016/059329, filed Apr. 26, 2016, published as WO2016174048 A1 on Nov. 3, 2016, titled "REDUCED PRESSURE APPARATUS AND METHODS."

Figure 1B:
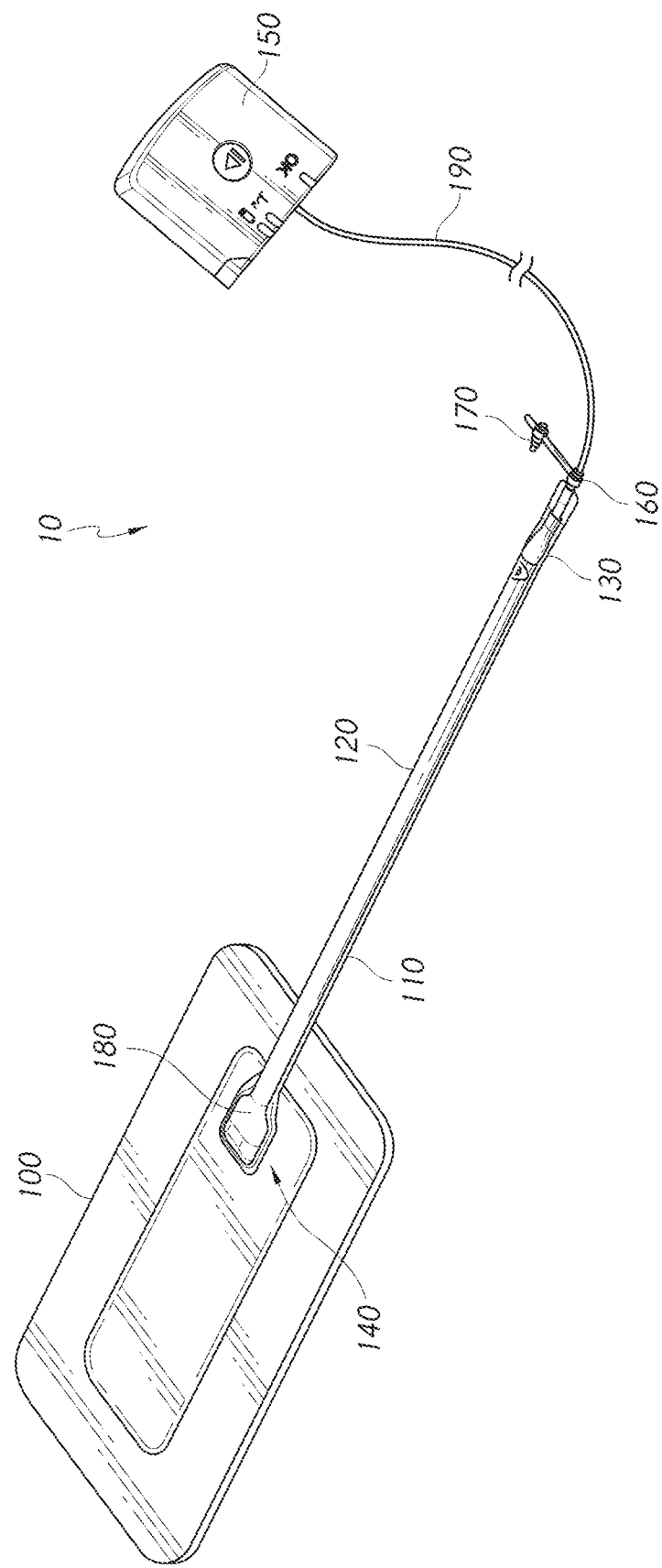
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound.

Application of negative pressure may be applied until a desired level of healing of the wound is achieved. In some embodiments, the pump can be miniaturized and portable, although larger conventional pumps may also be used with the dressing 100. In some embodiments, the pump may be attached or mounted onto or adjacent the dressing 100.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include a cover layer for positioning over the layers of the wound dressing. The cover layer can be the upper most layer of the dressing. In some embodiments, the wound dressing can include a second cover layer for positioning over the layers of the wound dressing and any of the integrated components. The second cover layer can be the upper most layer of the dressing or can be a separate envelope that encloses the integrated components of the topical negative pressure system.

Figure 2A:
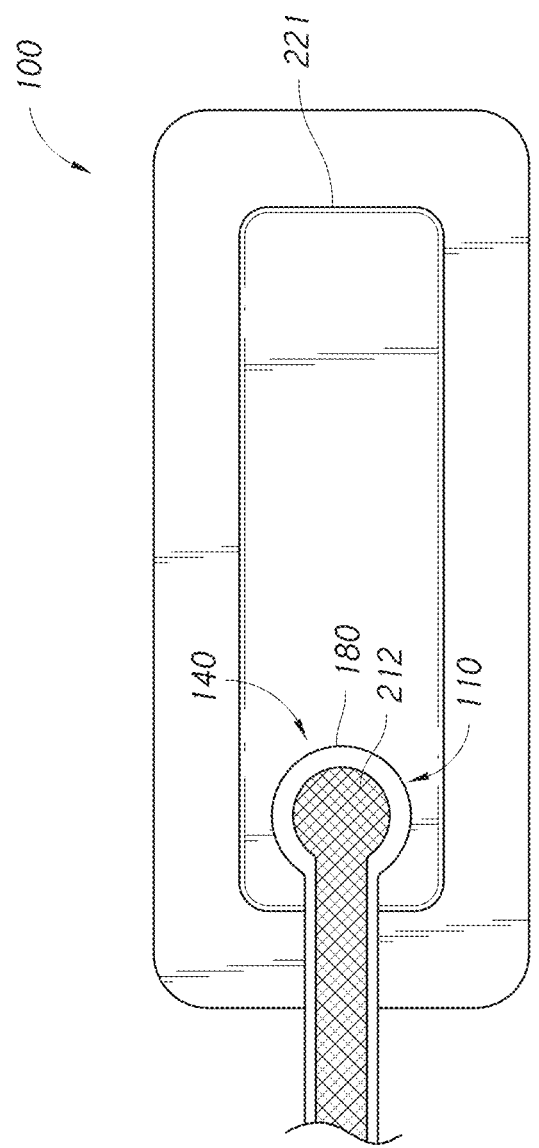
FIG. 2A illustrates an embodiment of a negative pressure wound treatment system employing a flexible fluidic connector and a wound dressing capable of absorbing and storing wound exudate.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 100 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 2B:
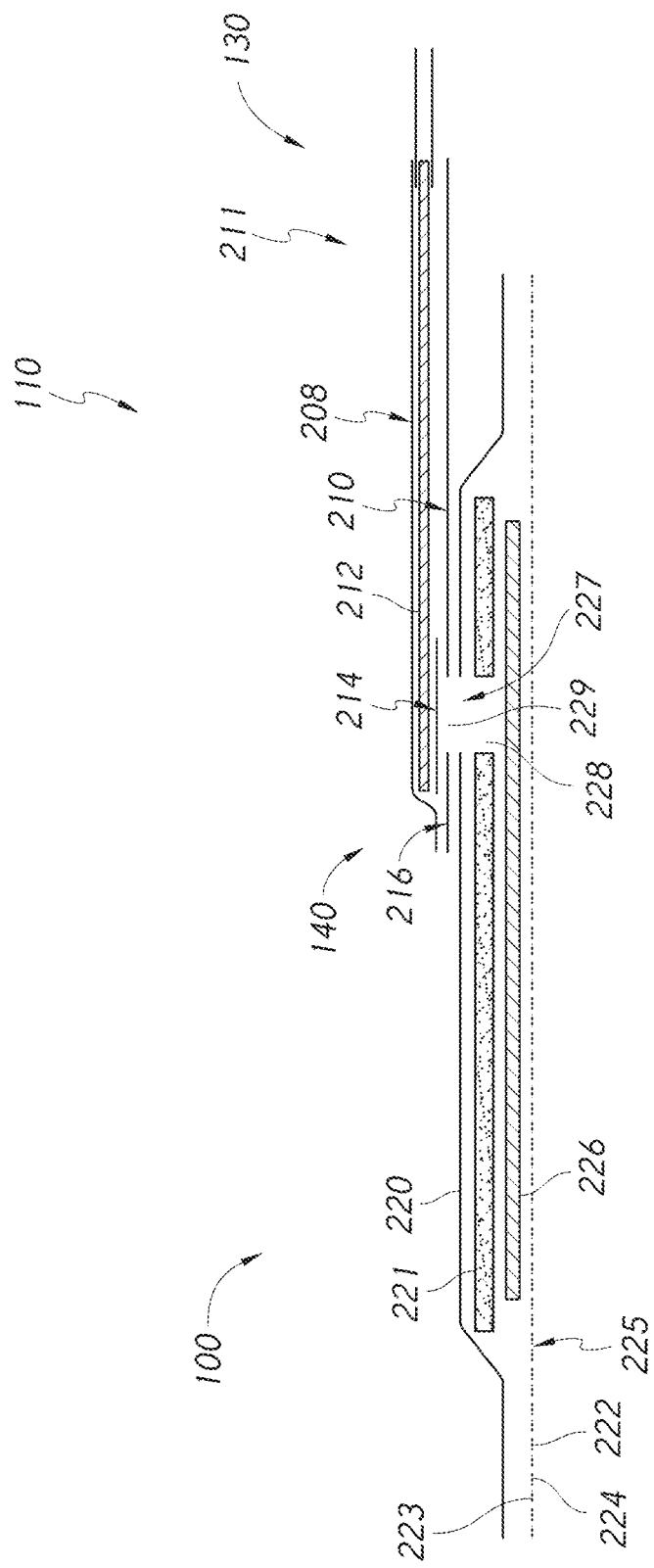
FIG. 2B illustrates a cross section of an embodiment of a fluidic connector connected to a wound dressing.

FIG. 2B illustrates a cross-section through a wound dressing 100 similar to the wound dressing 100 as shown in FIG. 1B and described in International Patent Publication WO2013175306 A2, filed May 22, 2013, entitled "APPARATUSES AND METHODS FOR NEGATIVE PRESSURE WOUND THERAPY", the disclosure of which is hereby incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally, should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in US Patent Publication 2015/0190286 A1, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 110, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 (described below) may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments, a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments, the upper surface and the lower surface may be formed from the same piece of material. In some embodiments, the sealing surface 216 may comprise at least one aperture 229 therein to communicate with the wound dressing. In some embodiments, the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected to the sealing surface 216. The filter 214 is configured to substantially prevent wound exudate from entering the bridge.

Some embodiments may further comprise an optional second fluid passage positioned above the first fluid passage 212. For example, some embodiments may provide for an air leak may be disposed at the proximal end of the top layer 208 that is configured to provide an air path into the first fluid passage 212 and dressing 100 similar to the suction adapter as described in U.S. Pat. No. 8,801,685, filed Dec. 30, 2011, entitled "APPARATUSES AND METHODS FOR NEGATIVE PRESSURE WOUND THERAPY" the disclosure of which is hereby incorporated by reference in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 3A:
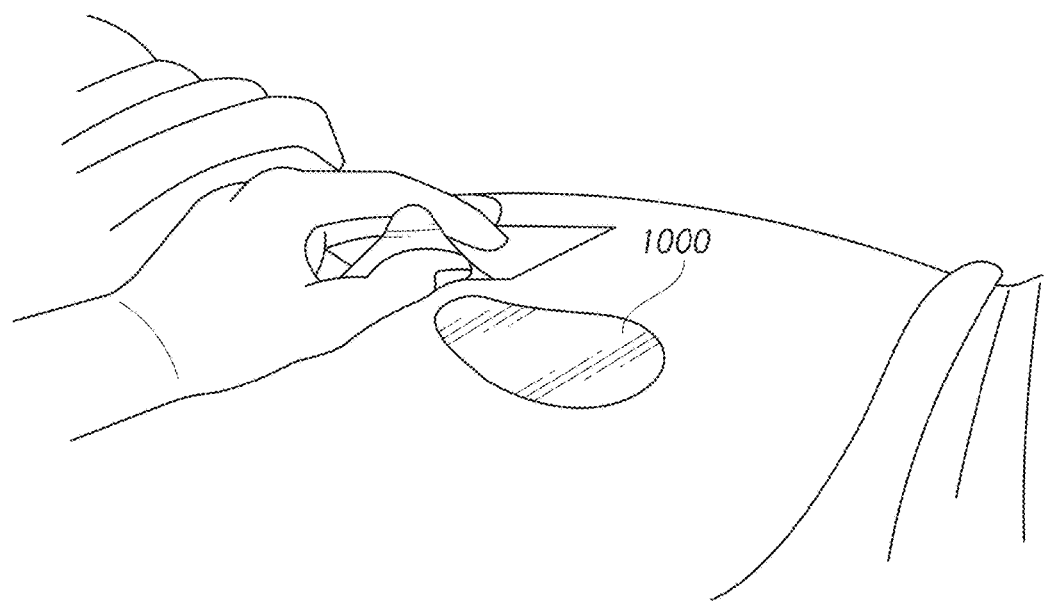
FIGS. 3A-D illustrate the use and application of an embodiment of a wound treatment system onto a patient.

FIGS. 3A-D illustrate the use of an embodiment of a negative pressure therapy wound treatment system being used to treat a wound site on a patient. FIG. 3A shows a wound site 1000 being cleaned and prepared for treatment. Here, the healthy skin surrounding the wound site 1000 is preferably cleaned and excess hair removed or shaved. The wound site 1000 may also be irrigated with sterile saline solution if necessary. Optionally, a skin protectant may be applied to the skin surrounding the wound site 1000. If necessary, a wound packing material, such as foam or gauze, may be placed in the wound site 1000. This may be preferable if the wound site 1000 is a deeper wound.

Figure 3B:
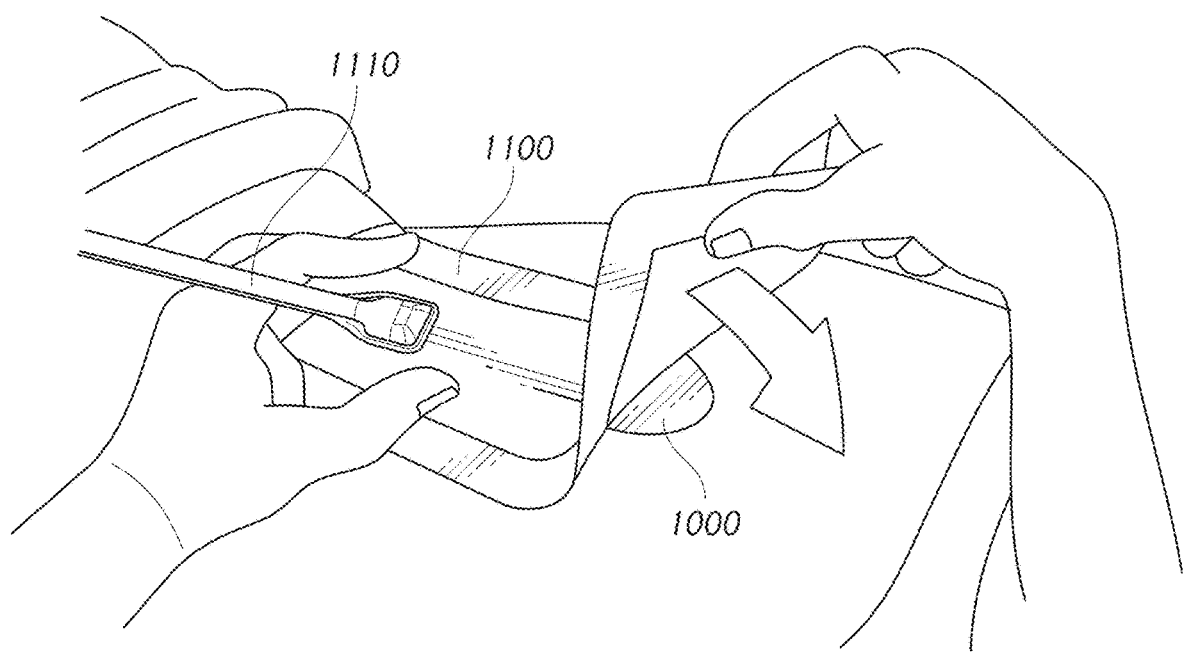

After the skin surrounding the wound site 1000 is dry, and with reference now to FIG. 3B, the wound dressing 1100 may be positioned and placed over the wound site 1000. Preferably, the wound dressing 1100 is placed with the wound contact layer over and/or in contact with the wound site 1000. In some embodiments, an adhesive layer is provided on the lower surface of the wound contact layer, which may in some cases be protected by an optional release layer to be removed prior to placement of the wound dressing 1100 over the wound site 1000. Preferably, the dressing 1100 is positioned such that the fluidic connector 1110 is in a raised position with respect to the remainder of the dressing 1100 so as to avoid fluid pooling around the port. In some embodiments, the dressing 1100 is positioned so that the fluidic connector 1110 is not directly overlying the wound, and is level with or at a higher point than the wound. To help ensure adequate sealing for TNP, the edges of the dressing 1100 are preferably smoothed over to avoid creases or folds.

Figure 3C:
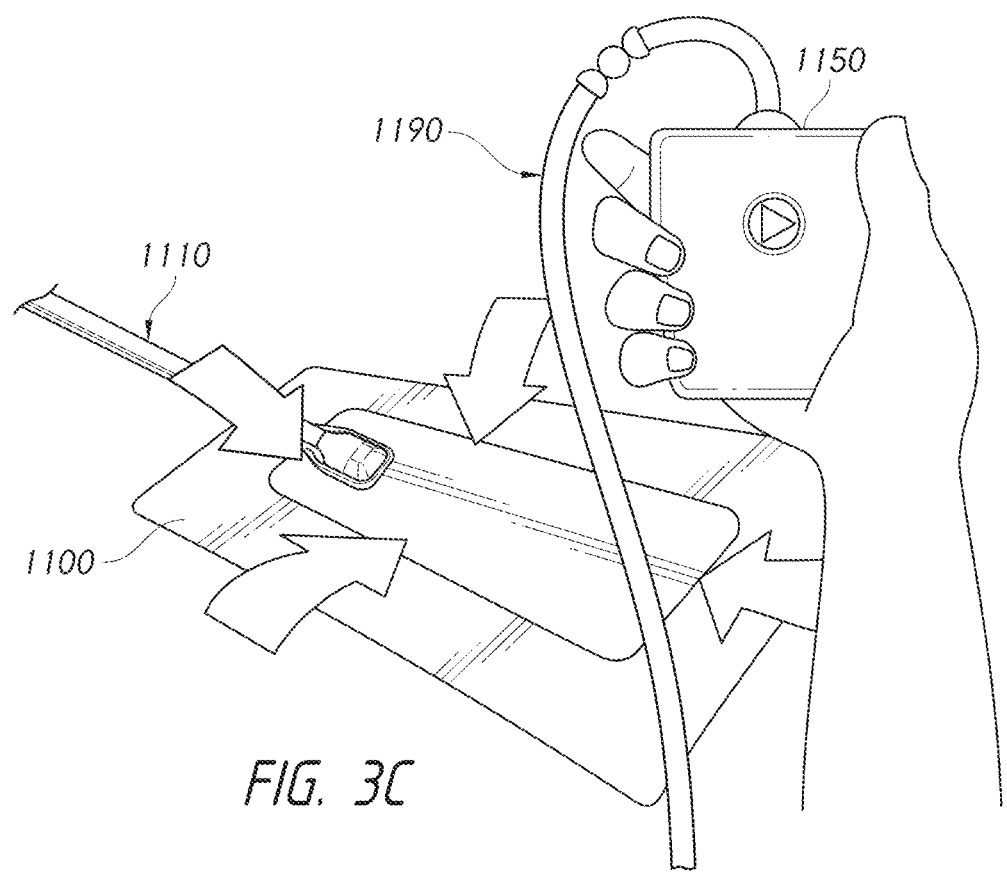

With reference now to FIG. 3C, the dressing 1100 is connected to the pump 1150. The pump 1150 is configured to apply negative pressure to the wound site via the dressing 1100, and typically through a conduit. In some embodiments, and as described herein, a fluidic connector 1110 may be used to join the conduit 1190 from the pump to the dressing 1100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments, the conduit may comprise a fluidic connector. It is expressly contemplated that a conduit may be a soft bridge, a hard tube, or any other apparatus which may serve to transport fluid. Upon the application of negative pressure with the pump 1150, the dressing 1100 may in some embodiments partially collapse and present a wrinkled appearance as a result of the evacuation of some or all of the air underneath the dressing 1100. In some embodiments, the pump 1150 may be configured to detect if any leaks are present in the dressing 1100, such as at the interface between the dressing 1100 and the skin surrounding the wound site 1000. Should a leak be found, such leak is preferably remedied prior to continuing treatment.

Figure 3D:
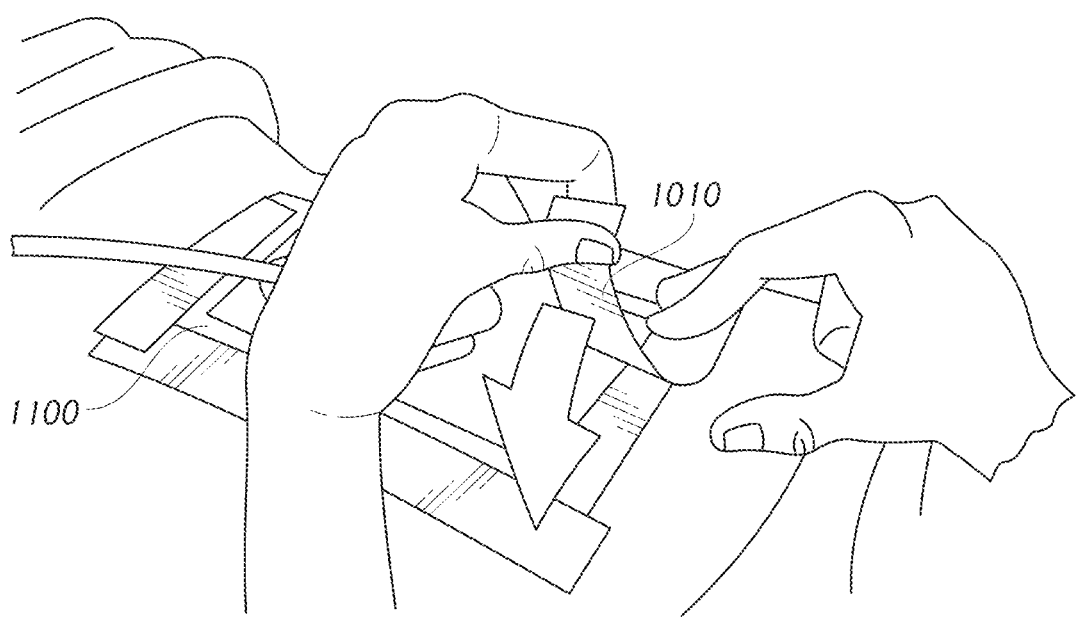

Turning to FIG. 3D, additional fixation strips 1010 may also be attached around the edges of the dressing 1100. Such fixation strips 1010 may be advantageous in some situations so as to provide additional sealing against the skin of the patient surrounding the wound site 1000. For example, the fixation strips 1010 may provide additional sealing for when a patient is more mobile. In some cases, the fixation strips 1010 may be used prior to activation of the pump 1150, particularly if the dressing 1100 is placed over a difficult to reach or contoured area.

Treatment of the wound site 1000 preferably continues until the wound has reached a desired level of healing. In some embodiments, it may be desirable to replace the dressing 1100 after a certain time period has elapsed, or if the dressing is full of wound fluids. During such changes, the pump 1150 may be kept, with just the dressing 1100 being changed.

In certain embodiments, such as described above in relation to FIG. 2B, fluid (for example, wound exudate) is handled by the dressing 100 by passing through the perforated wound contact layer 222, into the transmission layer 226, and is then absorbed and retained by the absorbent layer 221. Fluid is then able to evaporate through the breathable backing layer 220. However, in some embodiments, wound dressings such as those described above can have a lifetime of just over 3 days when tested on a standard in vitro wound model. During these tests the dressing is considered to be functioning successfully if it maintains the target vacuum level (e.g., −80 mmHg) and mobile liquid is not visible within the dressing during testing or, at the time of vacuum failure, upon removal. The failure mode can be caused by a blocking of the semi-permeable membrane of the fluidic connector by the input liquid.

It is desirable that the dressing offers no means for the wet absorbent layer to block the fluid pathway to the fluidic connector prior to the dressing becoming full to its liquid capacity. Some embodiments of dressings fail at 3 days, for example due to blockage of the fluid pathway to the fluidic connector. The absorbent layer can preferentially saturate at or near the port prior to filling the remainder of the dressing, thereby leading to blockages before the dressing is saturated. Therefore, as described above, it may be desirable to ensure that certain other areas of the absorbent layer are preferentially saturated before the areas near the port or fluidic connector.

In some embodiments, fluid saturation of the absorbent layer near the port may be impeded or controlled by utilizing an absorbent layer divided into two or more physically separate portions and/or units. For example, an absorbent layer may comprise at least a first portion and a physically separate second portion as described herein. These two or more physically separate portions may be positioned within the same plane, such as the same horizontal plane when the wound dressing is considered to have a vertical height defined by the thicknesses of its layers and the length and width of the dressing are parallel to the horizontal plane.

As used herein and throughout the specification, the term "physically separate" is used to refer to two portions or parts that are not integrally connected with one another.

The terms parts, pieces, units, and/or portions of absorbent material refer to the physically separate pieces of material that make up the absorbent layer and these terms can be used interchangeably herein and throughout the specification. Parts, units, or portions that are physically separate, may however touch or come into contact with one another. For example, two physically separate portions of an absorbent layer may contact each other along a side or edge, but may not be integrally formed or substantially connected together.

In some embodiments, physically separate parts or portions may comprise portions that are separately formed from one another. However, in some other embodiments absorbent units may be portions of the same initial whole that have been cut apart or otherwise substantially separated. In these embodiments, a relatively small amount of remaining material may connect the otherwise physically separate units, however such material does not significantly contribute to or create a fluid communication pathway between the physically separate portions. In some embodiments, a silicone gel can be used to inhibit fluid movement between the units. In other embodiments, the physically separate units can be in intimate contact with the dressing layers above or below the units, for example, the spacer layers to inhibit fluid movement between the units.

A given portion of the absorbent layer which is absorbing wound exudate may continue to do so, and said exudate may be impeded in tracking or flowing, compared to the movement in a single piece absorbent layer, into an adjacent portion of the absorbent layer. The flow of the fluid into the adjacent portions is dependent on the flow of the fluid through the layer below the absorbent layer, for example the spacer or transmission layer. As the fluid moves through the spacer layer, the portion of absorbent in contact with the spacer layer containing fluid will begin to become saturated. As that portion becomes saturated fluid can begin to track to each individual unit adjacent or next to that unit. The adjacent portion may then absorb fluid at least via the given portion of the absorbent layer as it becomes saturated, thereby creating additional fluid flow pathways to other adjacent portions. Accordingly, the portions of the absorbent layer adjacent to the given portion may begin to absorb fluid, such as wound exudate, before fluid is able to flow or track freely to an adjacent portion that is closer to the port or fluidic connector that is supplying negative pressure to the wound dressing 400. Accordingly, the physically separated units of the absorbent layer can limit tracking of fluid through the absorbent layer to each individual unit. Thus, the absorbent layer 421 may be able to absorb more fluid before the port 110 becomes blocked or occluded by exudate as compared with a wound dressing that comprises a single piece absorbent layer.

Figure 4A:
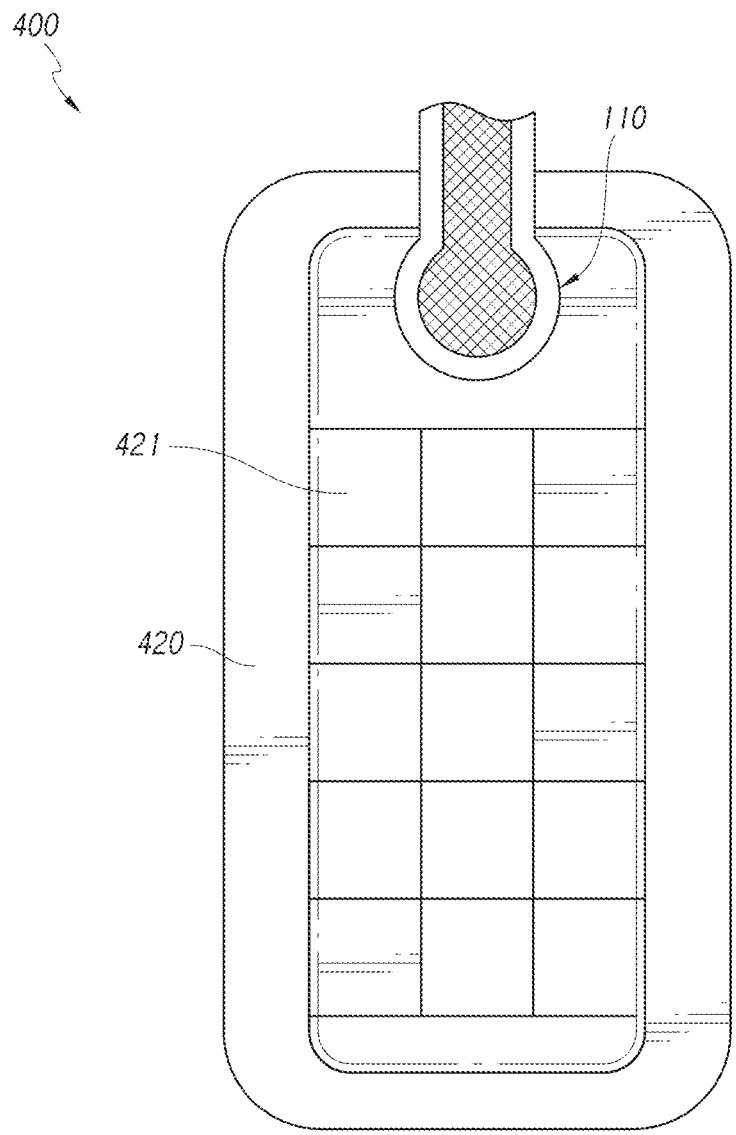
FIG. 4A illustrates a top view of an embodiment of a negative pressure wound treatment system employing an absorbent layer formed from physically separated portions and/or units of absorbent material within a wound dressing capable of absorbing and storing wound exudate.

FIG. 4A illustrates a top view of an embodiment of a negative pressure wound treatment system employing an absorbent layer formed from separate units of absorbent material within a wound dressing capable of absorbing and storing wound exudate. FIG. 4A illustrates an embodiment of a negative pressure wound treatment system employing a wound dressing 400 capable of absorbing and storing wound exudate. In some embodiments, the wound dressing can utilize an absorbent pad 421 cut into smaller units and the units or portions can be physically separated to assist with flexibility, conformability, and/or fluid handling of the dressing. In some embodiments, the absorbent layer can be formed of physically separated units of absorbent material. As used herein, the cut, separated, or physically separated absorbent material of the absorbent layer can be used interchangeably and refer to an absorbent layer that includes multiple pieces of absorbent material provided adjacent to each other to form the absorbent layer of the dressing with functions similar to the absorbent layer 221 described with reference to FIG. 2A-2B.

Figure 4B:
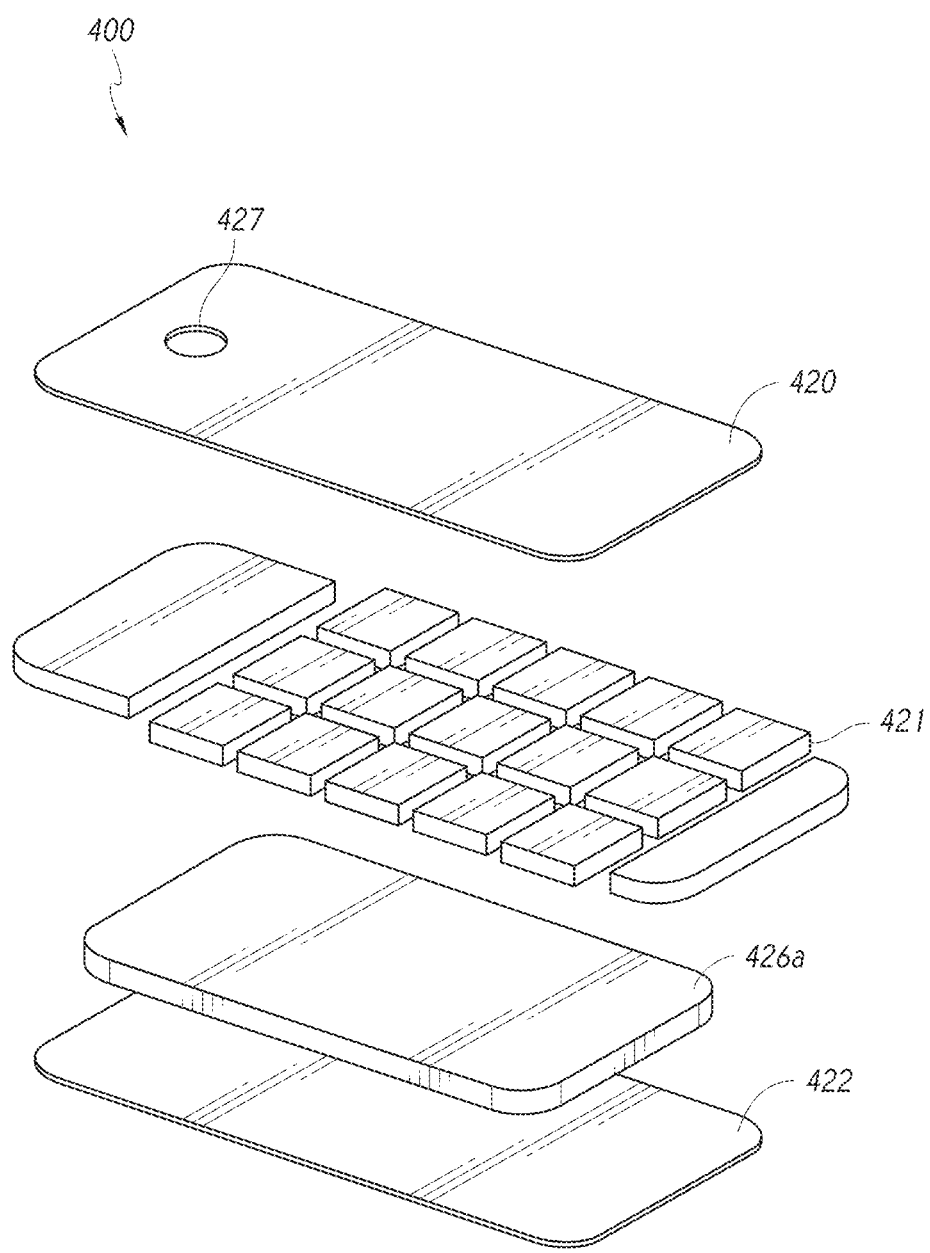
FIG. 4B illustrates layers of an embodiment of a negative pressure wound treatment system employing an absorbent layer formed from physically separated portions and/or units of absorbent material within a wound dressing capable of absorbing and storing wound exudate.
Figure 4C:
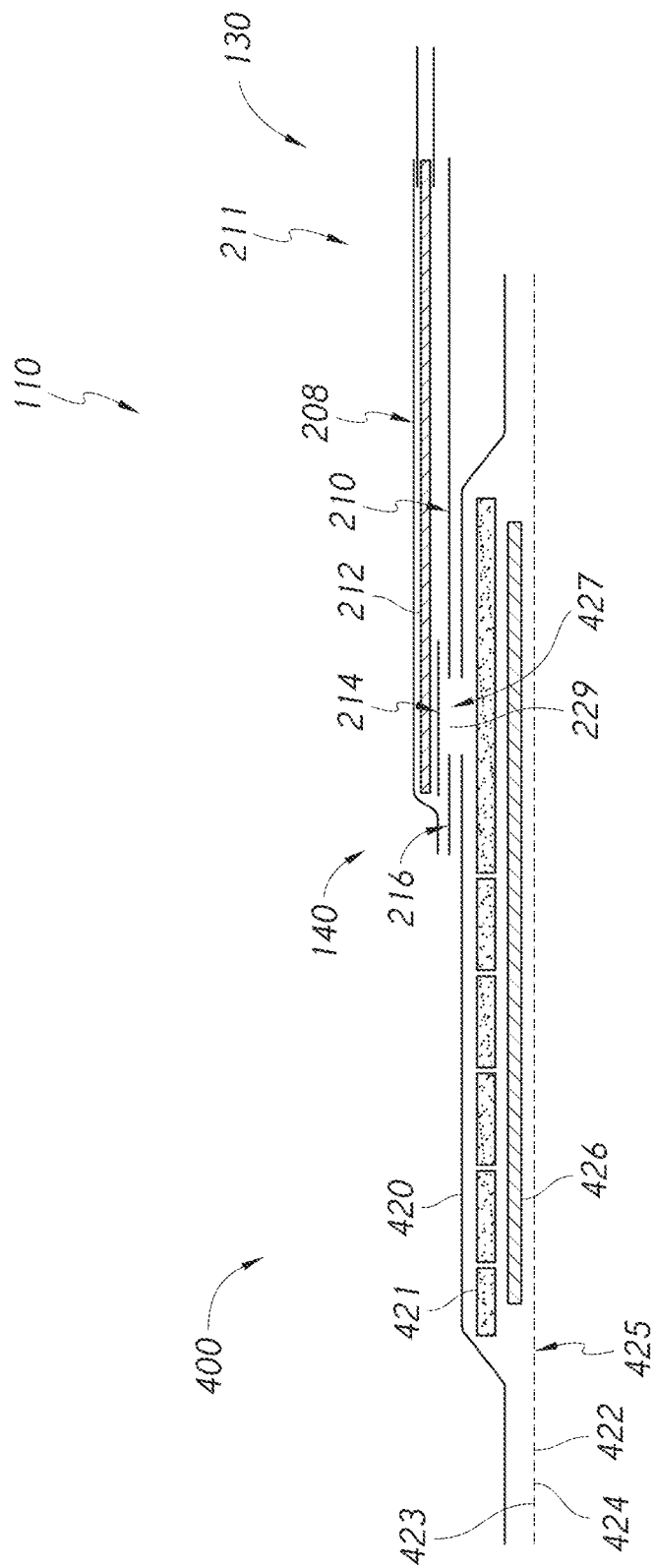
FIG. 4C illustrates a cross sectional side view of a negative pressure wound treatment system employing an absorbent layer formed from physically separated portions and/or units of absorbent material within a wound dressing capable of absorbing and storing wound exudate.
Figure 7:
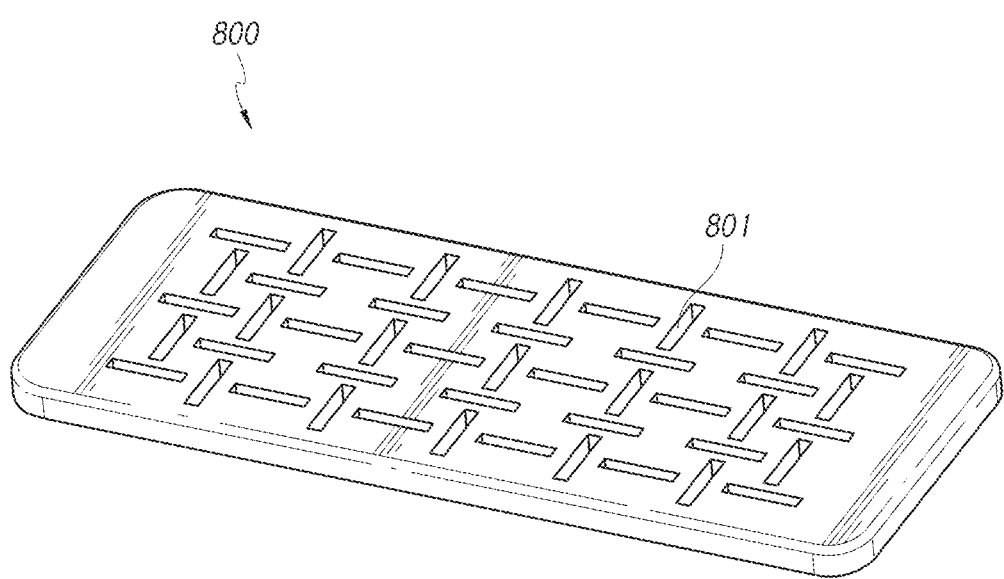
FIG. 7 illustrates an embodiment of a dressing layer with slits or cutouts for use within a wound dressing capable of absorbing and storing wound exudate.
Figure 8A:
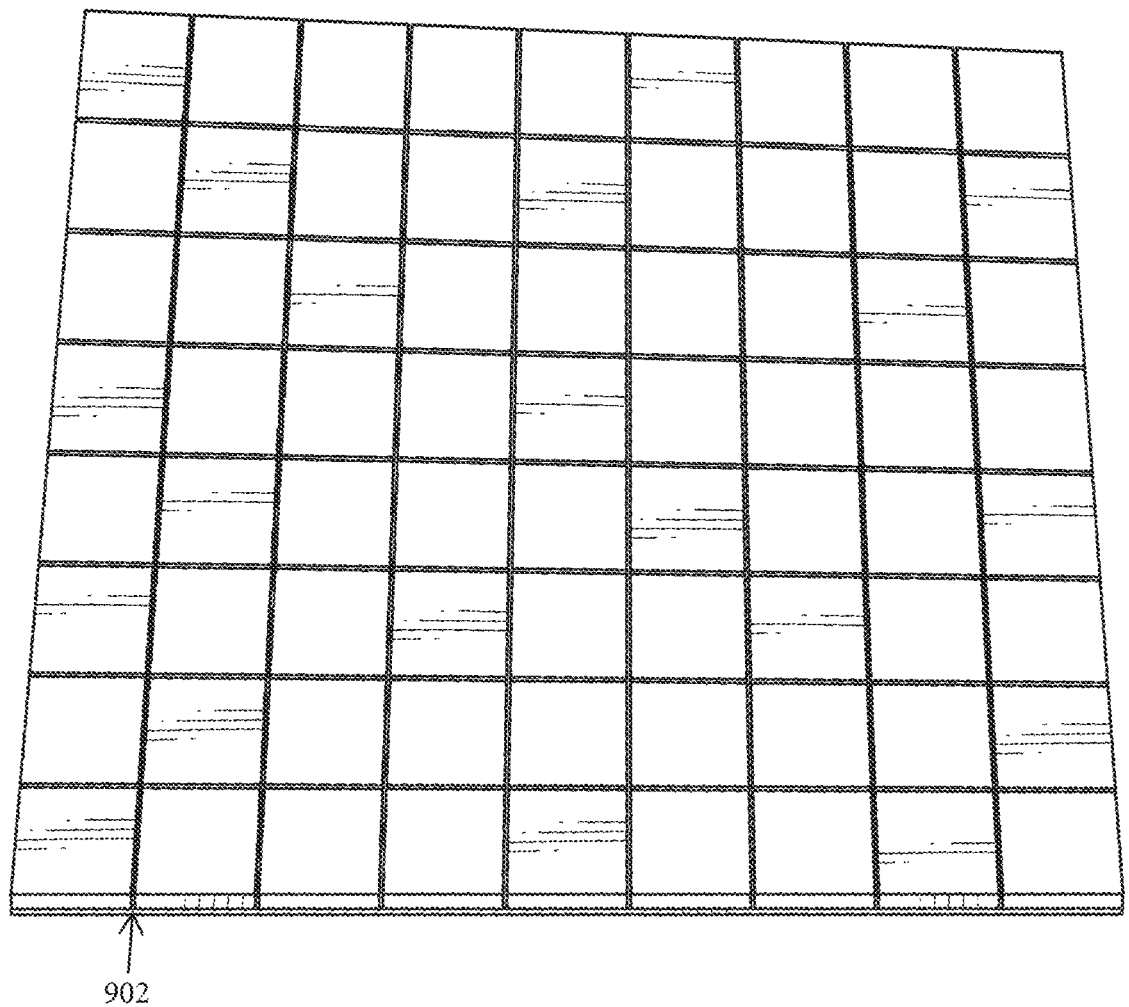
FIGS. 8A-8D and 9A-9C illustrate embodiments of geometric shapes for use in a layer formed from separated portions and/or units of material for use within a wound dressing capable of absorbing and storing wound exudate.
Figure 8B:
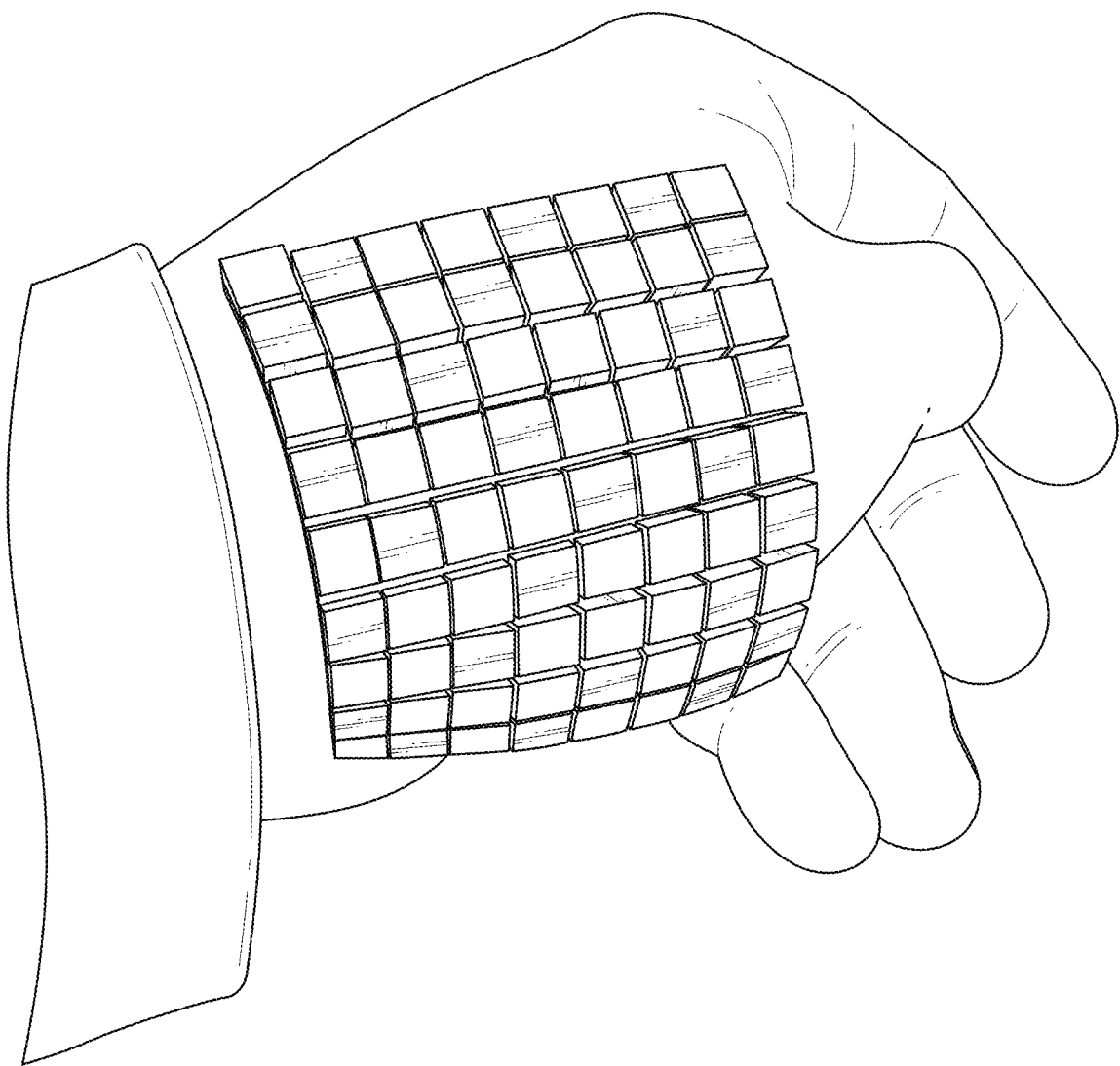
Figure 8C:
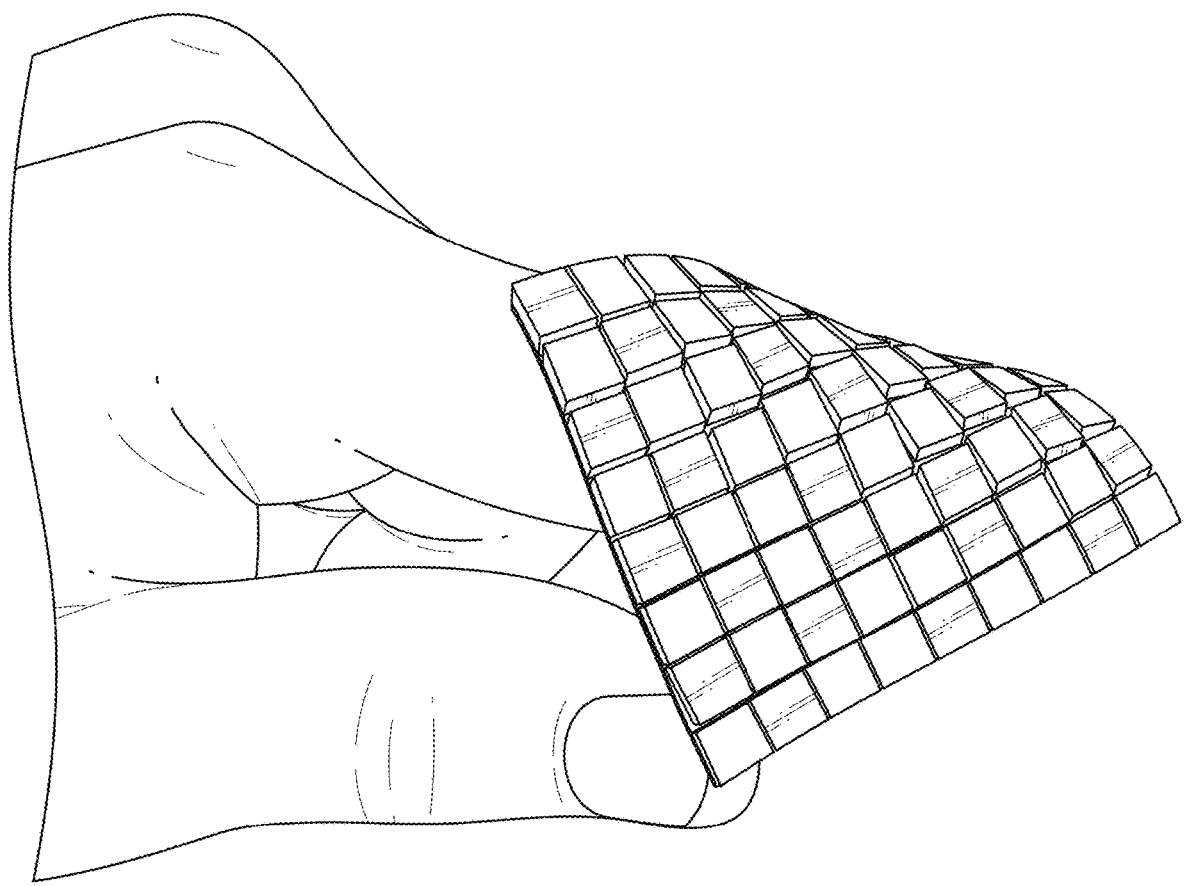
Figure 8D:
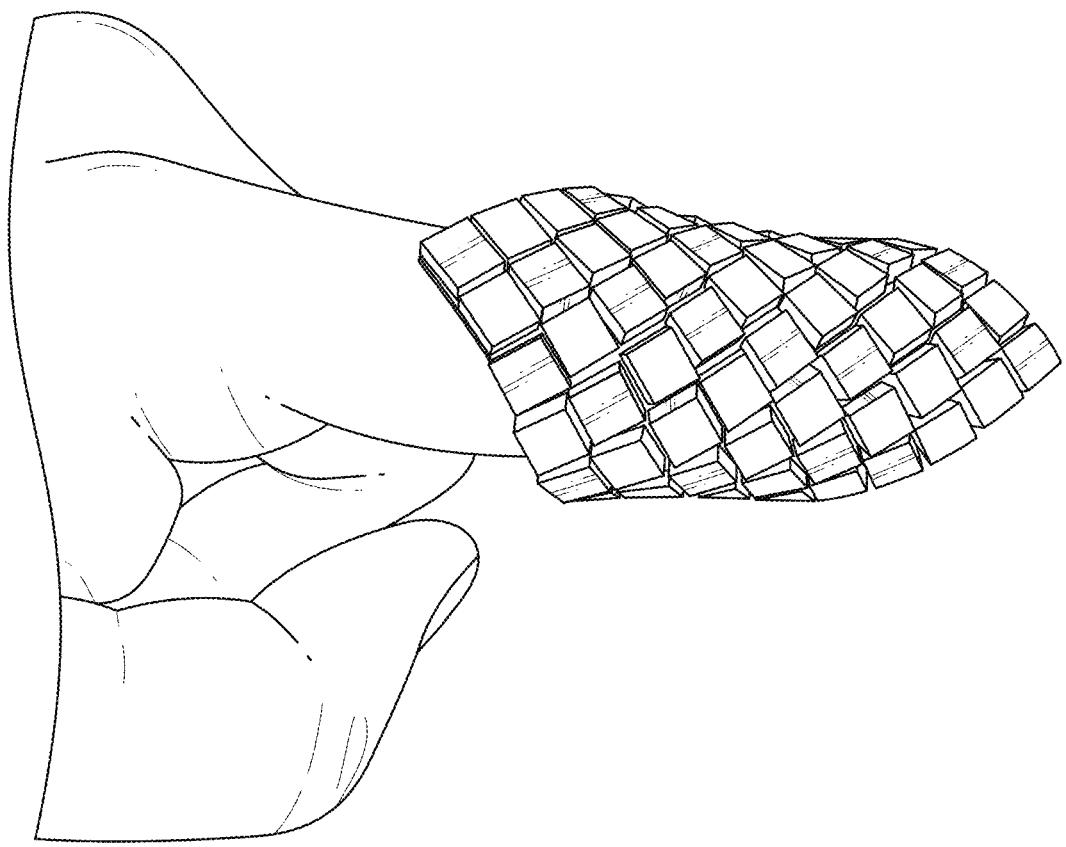

In some embodiments, the absorbent layer 421 can be formed from a 3 units by 5 units (width×length) configuration as illustrated in FIG. 4A. In some embodiments, the absorbent layer 421 can be formed from a 2 units by 5 units (width×length) configuration. The units of absorbent material can be in any arrangement and any number of units. In some embodiments, the absorbent layer can have different shaped and/or different sized units of absorbent material near the port 110 and/or furthest from the port 110 as shown in FIGS. 4A-4C. In some embodiments, the absorbent layer has units of absorbent material that are all the same size units as shown in FIG. 7. In some embodiments, the absorbent layer has units of absorbent material that are of various sizes. In other embodiments, the size and number of absorbent material portions may vary, provided that the portions extend across substantially the entire length and width of the absorbent layer 421. For example, more and/or smaller absorbent material portions, or fewer and/or larger absorbent material portions may comprise the absorbent layer 421 depending on the expected amount and/or flow rate of exudate from a wound which is to be treated.

FIGS. 4B and 4C illustrate layers of an embodiment of a negative pressure wound treatment system employing an absorbent layer formed from physically separated units of absorbent material within a wound dressing capable of absorbing and storing wound exudate. FIG. 4C illustrates a cross sectional side view of a negative pressure wound treatment system employing units of absorbent material within a wound dressing capable of absorbing and storing wound exudate. Unless otherwise noted, reference numerals and like-named components in FIG. 4C refer to components that are the same as or generally similar to the components of FIG. 2B.

As shown in FIGS. 4B and 4C, the wound dressing 400 can include a wound contact layer 422. The wound contact layer can be similar to the wound contact layer 222 described with reference to FIGS. 2A-2B. In some embodiments, the wound contact layer 422 can be a double-face coated (silicone-acrylic) perforated adhesive wound contact layer. A transmission layer 426a can be provided above the wound contact layer 422. The transmission layer 426a can be similar to the transmission layer 226 of the wound dressing described with reference to FIGS. 2A-2B. Absorbent layer 421 can be provided above the transmission layer 426a. The absorbent layer 421 can be similar to the absorbent layer 221 described with reference to FIGS. 2A-2B, however, the absorbent layer 421 can be physically separated into separate units of absorbent material as shown in FIGS. 4A-4C. In some embodiments, the absorbent layer 421 can be formed into shapes to enhance the dressing's ability to conform to a contoured surface of a patient's body and/or to improve and control the fluid handling of the dressing.

In some embodiments, the physically separated portions of the absorbent layer 421 can have a 1-10 mm gap separating each unit of absorbent material. This gap may be located along every side of a unit on which an adjacent unit of absorbent material is located. In some embodiments, the units can be squares, rectangles, circles, pentagons, hexagons, octagons, triangles, and/or any other regular or irregular shape.

A backing layer 420 sits over the absorbent layers 421. The backing layer 420 can include an orifice 427 that allows connection of the fluidic connector 140 to communicate negative pressure to the dressing. The backing layer 420 can be similar to the backing layer 220 described with reference to FIGS. 2A-2B. The perimeter of the backing layer 420 can seal to a perimeter of the wound contact layer 422 enclosing the transmission layer 426a and absorbent layers 421.

Figure 4D:
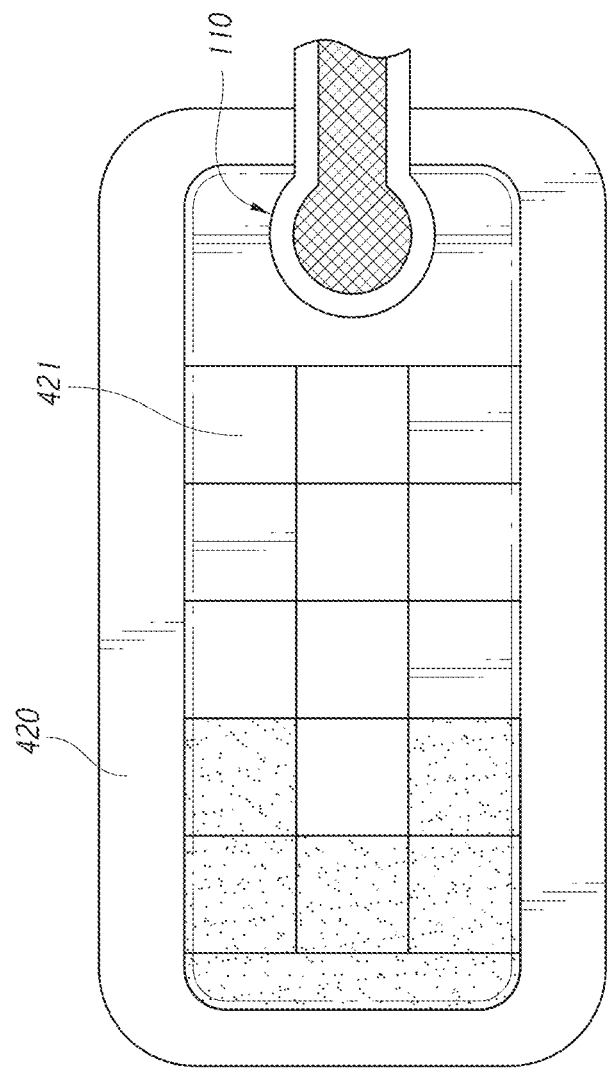
Figure 4F:
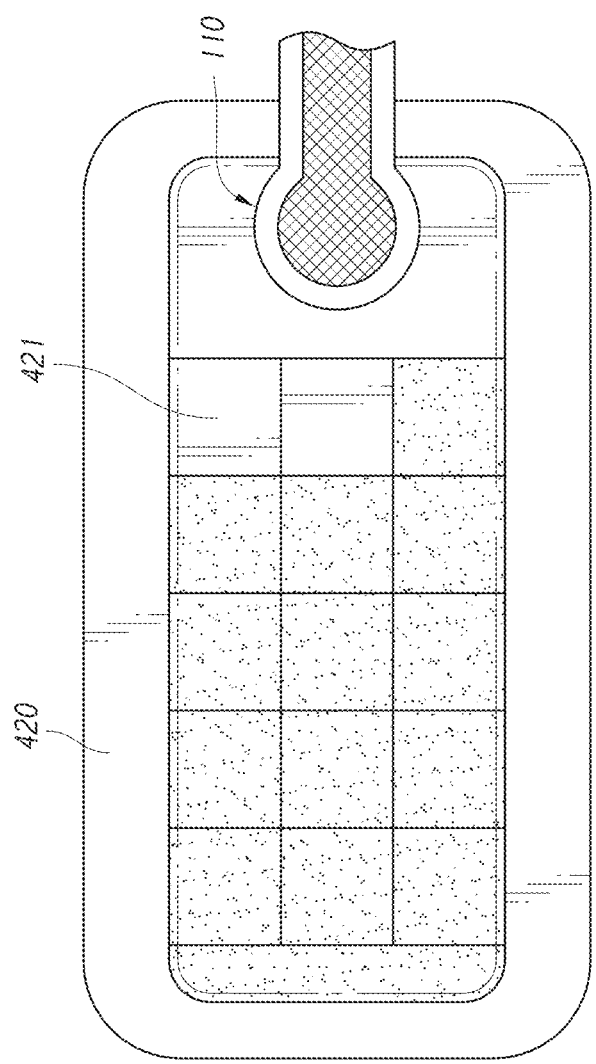

FIGS. 4D-4F illustrate embodiments of a wound dressing with an absorbent layer formed from physically separated units of absorbent material for use within a negative pressure wound treatment system.

FIG. 4D illustrates an embodiment of an absorbent layer made up of a plurality of units of absorbent material as fluid begins to enter the dressing. In some embodiments, when the port is placed at a location away from the wound, as negative pressure is applied, fluid begins to enter the absorbent layer at a location above the wound and furthest from the port as shown in FIG. 4D. As fluid continues to enter the dressing, the dressing will fill up unit by unit as the fluid tracks toward the port as illustrated in FIGS. 4E-4F.

In this way, fluid tracking through the absorbent layer 421, for example to the area of the absorbent layer underlying the port or fluidic connector 110 may be impeded, or otherwise reduced relative to a substantially similar wound dressing as described herein that does not include an absorbent layer comprising a plurality of separate portions.

In some embodiments, when negative pressure is applied to the dressing 400, the dressing 400 and/or backing layer 420 may collapse and the portions of the absorbent layer 421 may contact one another. In some other embodiments, the portions of the absorbent layer 421 may be in contact with each other prior to the application of negative pressure.

When the dressing is positioned so that the port is furthest from the wound, the physically separated units of the absorbent layer can control or slow fluid tracking to the port. In this way, the separate units of absorbent portions can assist in fluid distribution and handling throughout the absorbent layer. The physically separated units of absorbent material can be square shaped units as illustrated in FIGS. 4D-4F. Cutting the absorbent layer into shapes and separating them with a space between each unit can lead to a uniform uptake of fluid in the absorbent layer. The uniform uptake of fluid is accomplished by negating the ability of the fluid to track through the material layer up to the port. In some embodiments, a silicone gel can be used to inhibit fluid movement between the units. In other embodiments, the physically separate units can be in intimate contact with the dressing layers above or below the units, for example, the spacer layers to inhibit fluid movement between the units. The ability to impede or slow the fluid from tracking to the port can prevent prematurely blocking the port area and stopping therapy.

Figure 5A:
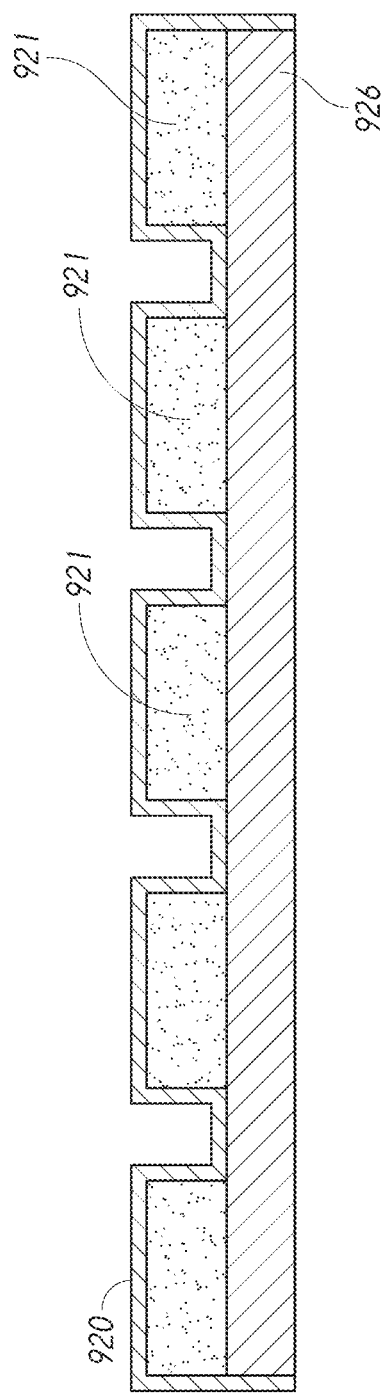
FIG. 5A illustrates a cross sectional view of physically separated portions and/or units of absorbent material within a wound dressing in a negative pressure wound treatment system.

FIG. 5A illustrates a cross sectional view of multiple pieces or units of absorbent material within a wound dressing in a negative pressure wound treatment system. FIG. 5A illustrates an embodiment of a cross section of the dressing with physically separated units of absorbent material forming the absorbent layer of the wound dressing. As illustrated in FIG. 5A, the units of absorbent material forming the absorbent layer can be positioned above a spacer layer 926 and can be covered by a top film or cover layer 920 that covers the absorbent and spacer layers of the dressing. The units of absorbent material forming the absorbent layer can be separated or spaced apart from each other as shown in FIG. 5A. The cover layer 920 can be similar to the cover layer 220, 420 described with reference to FIGS. 2A-B and FIGS. 4A-C but the cover layer 920 is vacuum formed into the space between the units of the absorbent layers 921. In some embodiments, the spacer layer 926 is positioned above a wound contact layer (not shown) similar to the wound contact layer 222 and 422 as described with reference to FIGS. 2A-B and FIGS. 4A-C respectively.

Figure 5B:
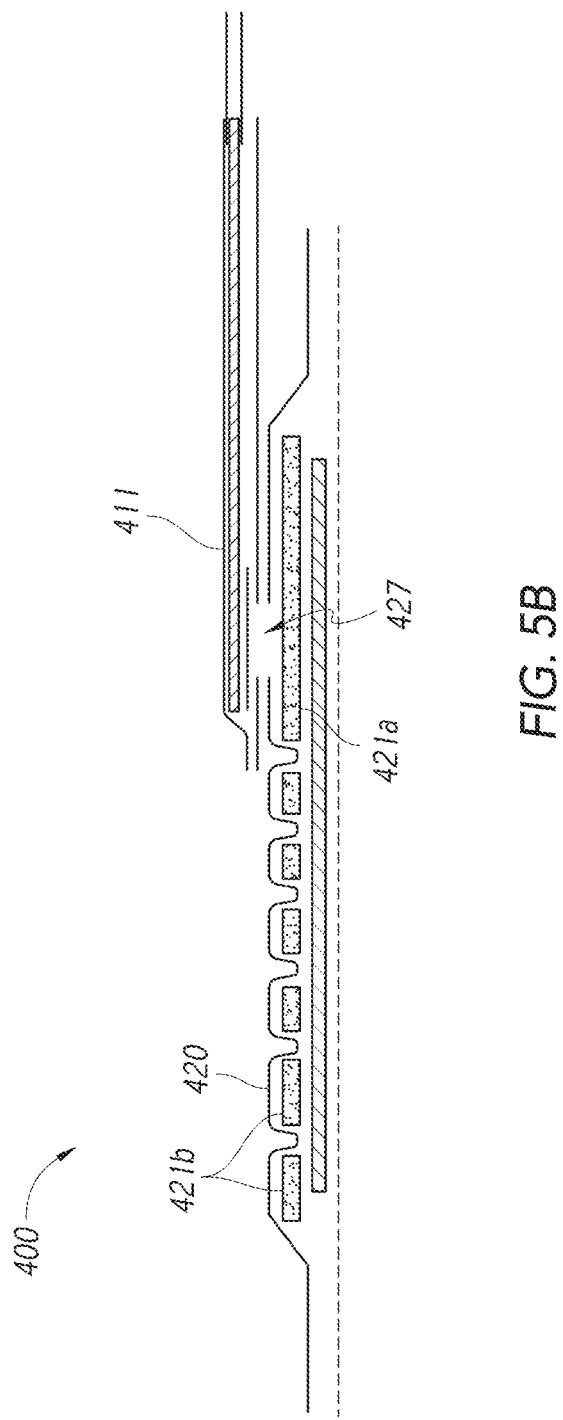
FIG. 5B illustrates a cross sectional side view of a negative pressure wound treatment system employing an absorbent layer formed from physically separated portions and/or units of absorbent material within a wound dressing capable of absorbing and storing wound exudate.

FIG. 5B shows a cross-section of an example wound dressing 400 according to some alternative embodiments, similar to the dressing described in FIG. 4C, with a backing layer 420 that extends at least partially into the spaces between the portions or units 421a, 421b of the absorbent layer 421. As described above, spaces between the portions or units of absorbent layer 421 may reduce or impede the ability of fluid to track through the absorbent layer 421 towards the port or fluid connector 411. In the example embodiment shown in FIG. 5B, the wound cover 420 may extend at least partially into the spaces between the portions 421a, 421b to thereby further reduce or prevent the formation of fluid flow pathways between adjacent portions 421a, 421b of the absorbent layer 421. As described above, for example with respect to the wound dressings of FIGS. 1A-2B, backing layer 420 may be fluid impermeable, and thus may not allow fluid to flow between adjacent portions 421a, 421b of the absorbent layer 421 where the backing layer extends into the spaces between said portions 421a, 421b.

The cover layer 420 may have a larger surface area than a similar backing layer 220 in order to account for folds or indentations that may be formed when the backing layer 420 at least partially extends into spaces between the portions 421a, 421b of the absorbent layer 421. In some embodiments the backing layer 420 may be vacuum formed to the absorbent layer 421 during assembly of the dressing 400.

Figure 6:
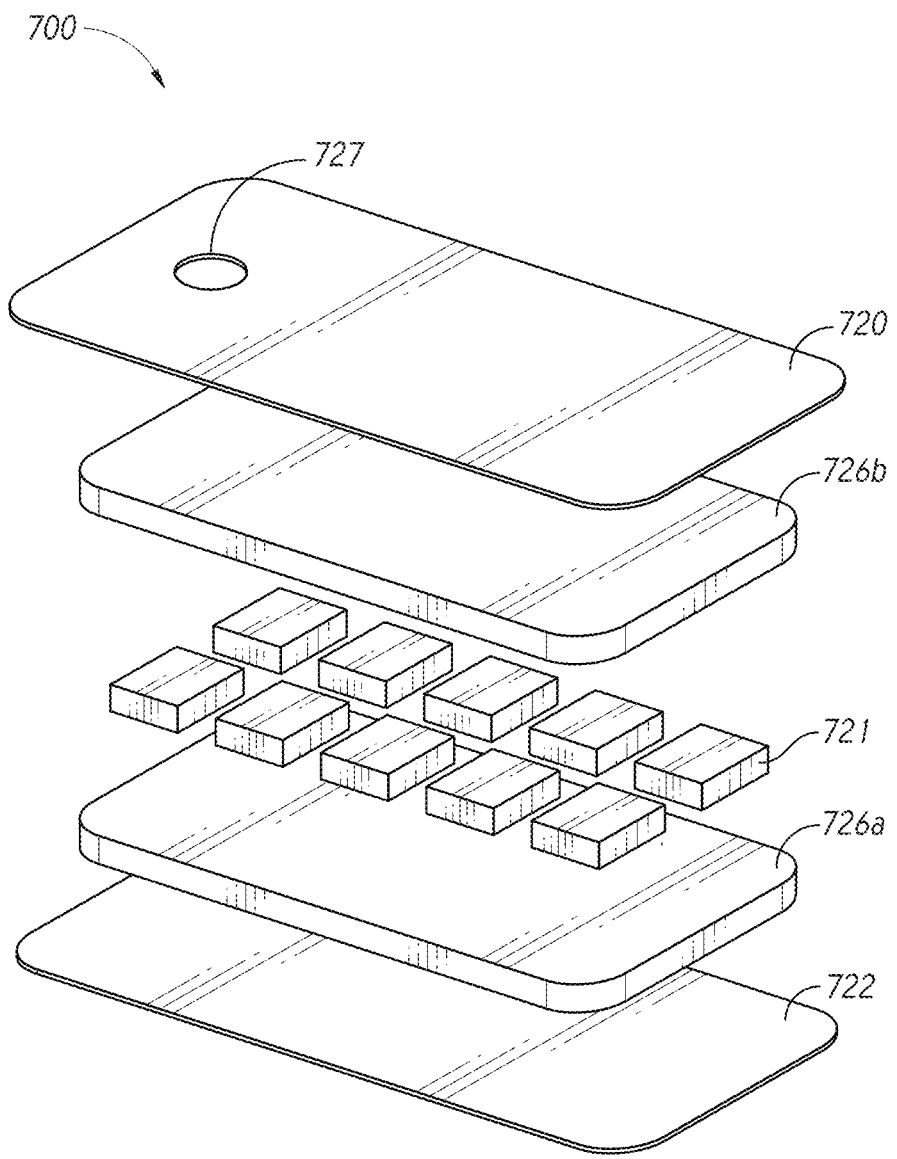
FIG. 6 illustrates layers of an embodiment of a negative pressure wound treatment system employing an absorbent layer formed from physically separated portions and/or units of absorbent material within a wound dressing capable of absorbing and storing wound exudate.

FIG. 6 illustrates layers of an embodiment of a negative pressure wound treatment system employing physically separated units of absorbent material within a wound dressing capable of absorbing and storing wound exudate. As shown in FIG. 6, the wound dressing 700 can include a wound contact layer 722. The wound contact layer can be similar to the wound contact layer 222 and 422 described with reference to FIGS. 2A-B and FIGS. 4A-C respectively. In some embodiments, the wound contact layer 722 can be a double-face coated (silicone-acrylic) perforated adhesive wound contact layer. A transmission layer 726a and absorbent layers 721 can be provided similar to the dressing described with reference to FIGS. 2A-2B but the absorbent layer is cut and physically separated into separate portions or units of absorbent material as shown in FIG. 6. The multiple units of absorbent material can be similar to the pieces or units of absorbent material described with reference to FIG. 5. The wound dressing 700 can include a second transmission layer 726b between the absorbent layer 721 and the cover layer or backing layer 720. A backing layer 720 sits over the second transmission layer 726b and the backing layer can include an orifice 727 that allows connection of the fluidic connector to communicate negative pressure to the dressing. In some embodiments, the first and second transmission layers 726a and 726b can over-border the units of the absorbent layer sandwiching or enclosing the units of the absorbent layer between. In some embodiments, the transmission layer or spacer layer can be a continuous piece of spacer layer that encircles and/or surrounds the units of the absorbent layer 721. Examples of such applications where additional disclosure relating to the preceding may be found in International Application No. PCT/EP2016/082353, titled "NEGATIVE PRESSURE WOUND THERAPY APPARATUS," filed Dec. 22, 2016, the disclosure of which is hereby incorporated by reference in its entirety.

FIG. 7 illustrates an embodiment of a dressing layer with slits or cutouts for use within a wound dressing capable of absorbing and storing wound exudate. In some embodiments, a wound dressing can include one or more layers of material 800 with slits and/or cutouts 801 that allow for the material layer to bend and flex to conform to the contours of the body of a patient. In some embodiments, an absorbent layer with slits and/or cutouts 801 can be used in place of the spaced units of absorbent material described in FIGS. 4A-4F, 5, and 6. In some embodiments, the absorbent layer with slits and/or cutouts 801 can aid transmission of negative pressure throughout the dressing by creating a more robust air path.

Figure 9A:
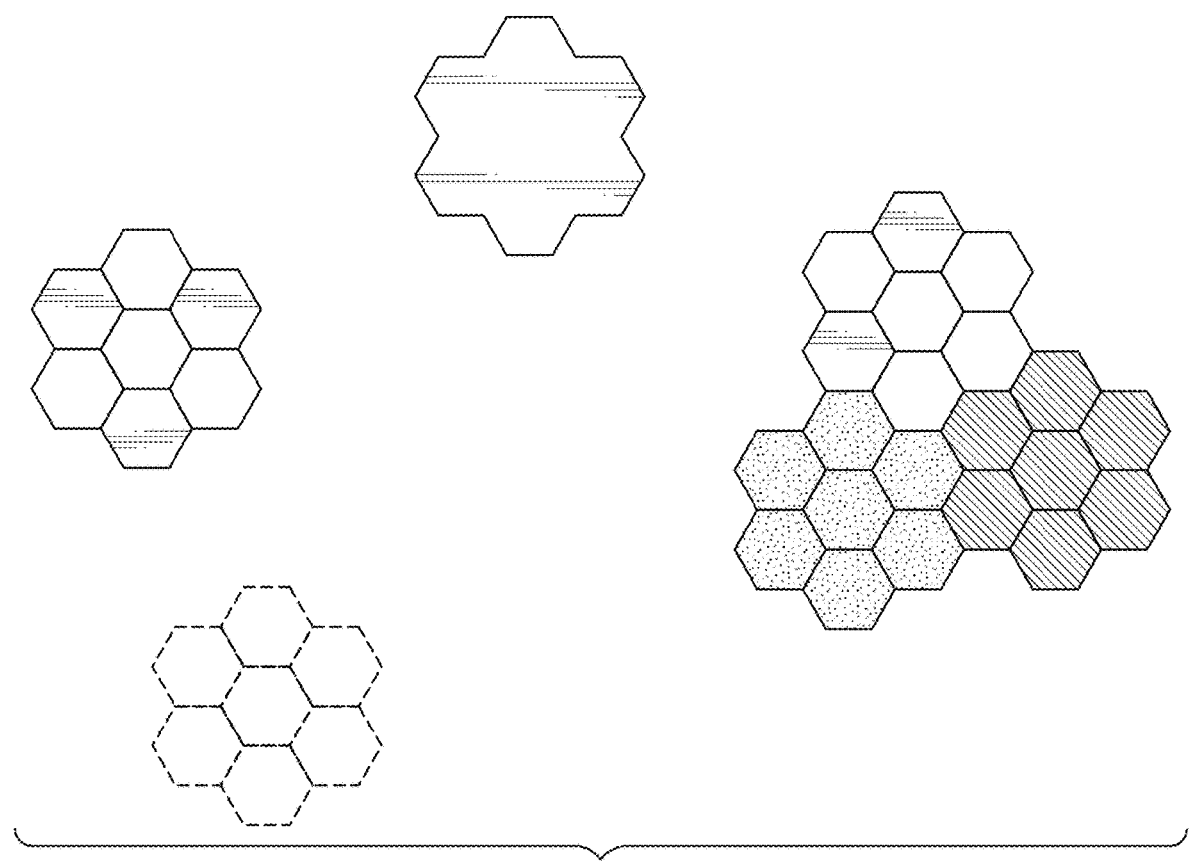
Figure 9B:
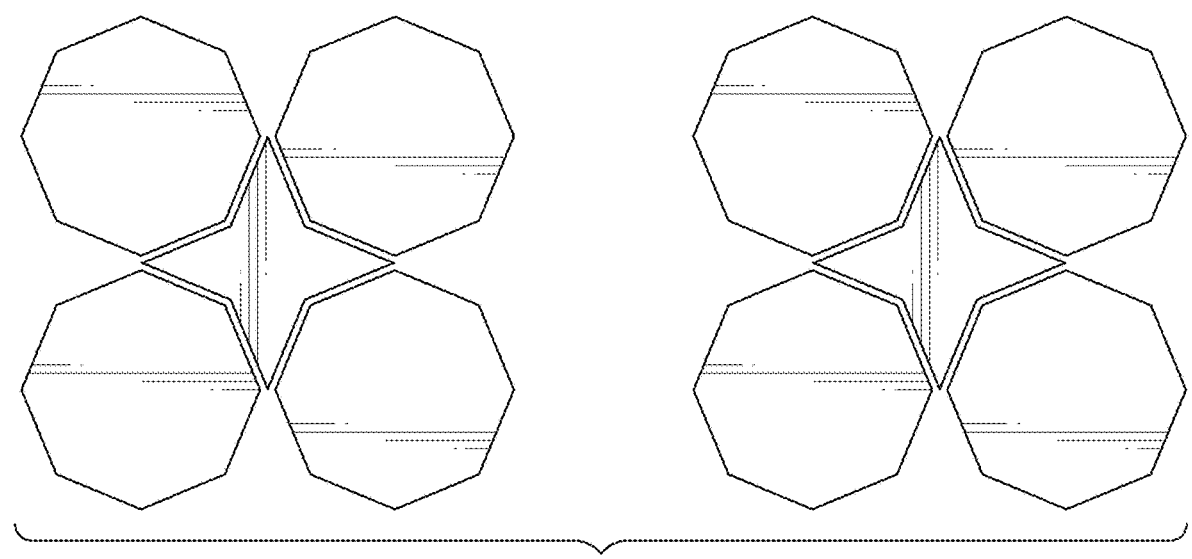
Figure 9C:
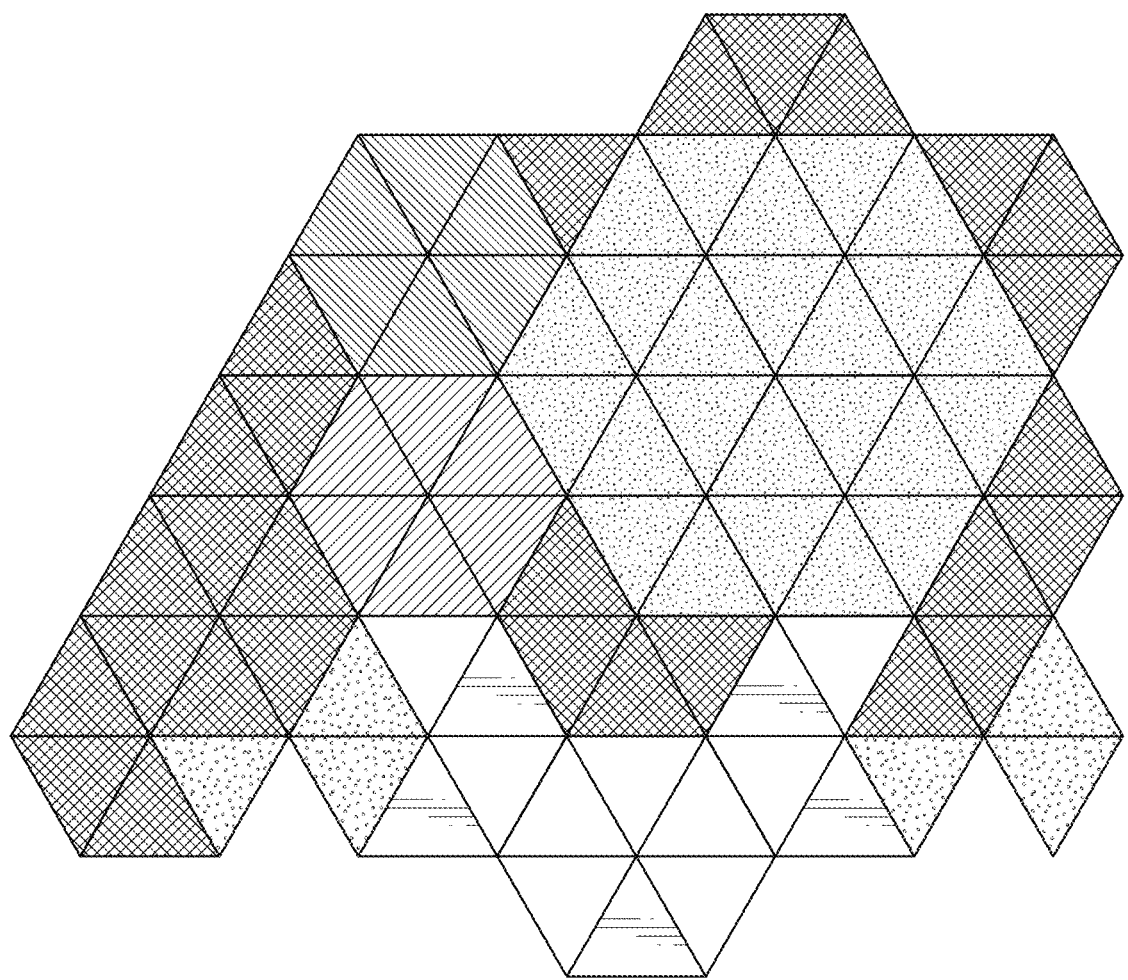

FIGS. 8A-8D and 9A-9C illustrate embodiments of geometric shapes that can be used for spaced units of absorbent material within a wound dressing capable of absorbing and storing wound exudate. FIGS. 8A-8D and 9A-9C illustrate embodiments of a negative pressure wound treatment system with shaped units of absorbent material within a dressing layer to allow increased conformability and flexibility to the wound dressing. The flexible dressing can utilize multiple units of absorbent material to form the absorbent layer and/or spacer layer that can conform to a contoured part of the body of a patient. In some embodiments, the spaced units of absorbent material can be formed from rectangular or square portions as shown in FIGS. 8A-8D. In some embodiments, the spaced units of absorbent material can be formed of shapes that tessellate including, but not limited to, a triangle, a hexagon, or an octagon as shown in FIGS. 9A-9C. In some embodiments, a hexagon shape can be used to allow the dressing layer to flex at various angles due to the shape.

In certain embodiments, such as described above in relation to FIG. 2B, fluid (for example, wound exudate) is handled by the dressing 100 by passing through the perforated wound contact layer 222, into the transmission layer 226, and is then absorbed and retained by the absorbent layer 221. Fluid is then able to evaporate through the breathable backing layer 220. As described previously, the failure mode of the dressing can be caused by a blocking of the semi-permeable membrane of the fluidic connector by the input liquid.

As described previously, it is desirable that the dressing offers no means for the wet absorbent layer to block the fluid pathway to the fluidic connector prior to the dressing becoming full to its liquid capacity. Some embodiments of dressings fail at 3 days, for example due to blockage of the fluid pathway to the fluidic connector. The absorbent layer can preferentially saturate at or near the port prior, thereby leading to blockages. Therefore, as described above, it may be desirable to ensure that certain other areas of the absorbent layer are preferentially saturated before the areas near the port or fluidic connector, or that the areas of the absorbent layer adjacent the port do not become saturated at all.

In some embodiments, the absorbent layer may comprise one or more portions configured to impede or block the fluid pathways therethrough. For example, an absorbent layer comprising a compressed portion configured to impede fluid flow therethrough can be used. In some embodiments this portion or portions may comprise the same material as the rest of the absorbent layer, however the portions may be compressed, for example during manufacturing, in order to impede the flow of fluid therethrough. In some other embodiments this portion or portions may comprise a second, different material than the rest of the absorbent layer that has a reduced flow rate as compared to the rest of the absorbent material.

Whereas the absorbent layer may comprise foam or another such absorbent material as described herein which allows for the absorption and flow of fluid, a compressed portion of the absorbent may have a structure which does not allow for, or impedes the absorption and/or flow of fluid therein. For example, in some embodiments a compressed portion may comprise the same material as the rest of the absorbent layer, but may have been subjected to pressure and/or heat during manufacturing in order to compress any voids or spaces in the material.

In some embodiments the compressed portion may serve to separate two or more uncompressed portions of the absorbent layer and impede the fluid flow between these uncompressed portions. Thus, in some embodiments, preferential fluid saturation of the absorbent layer may be impeded or controlled by utilizing an absorbent layer comprising a compressed portion which may divide the absorbent layer into two or more uncompressed portions.

Figure 10:
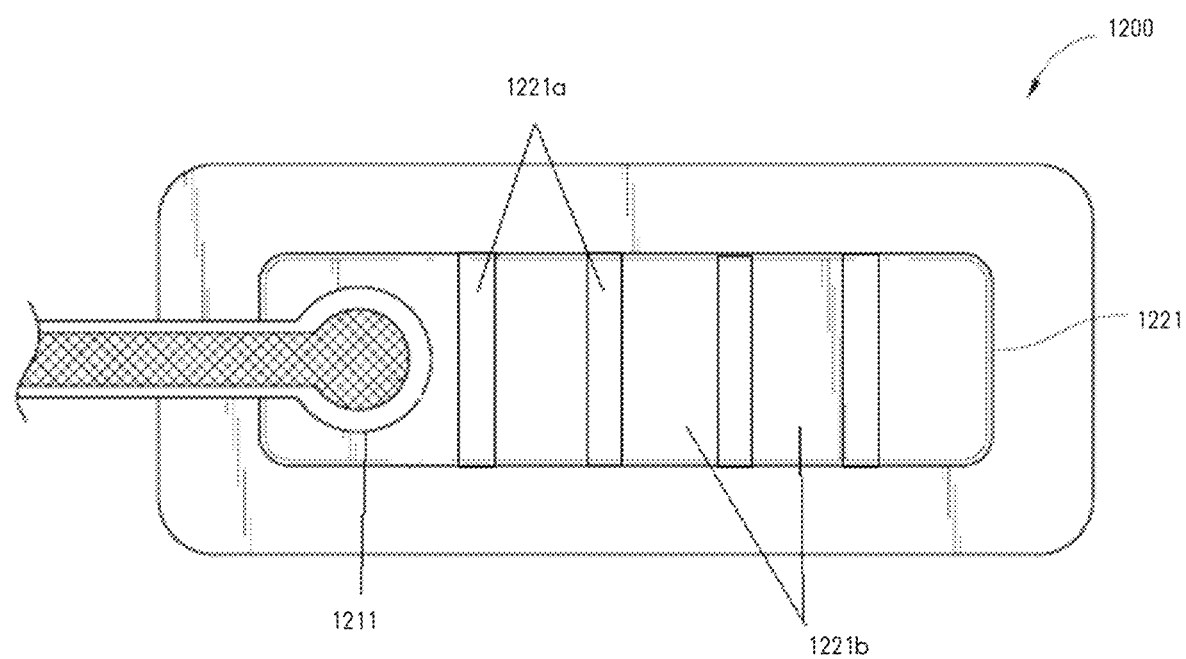
FIG. 10 illustrates a top view of an embodiment of a wound dressing capable of absorbing and storing wound exudate.

FIG. 10 shows a top view of a wound dressing 1200, similar to the dressings described in FIGS. 1A-2B. However, in this embodiment the absorbent layer 1221 comprises a plurality of compressed portions 1221a and absorbent, or uncompressed portions 1221b. In some embodiments one or more of the compressed portions 1221a may extend across an entire length or width of the absorbent layer, to thereby fluidically divide the portions of the absorbent layer adjacent to the compressed portion 1221a. In some embodiments where a compressed portion 1221a extends across the entire length or width of the absorbent layer 1221, a fluid communication pathway from the wound site to the fluidic connector 1211 through the absorbent layer 1221 may be fluidically interrupted by the compressed portions 1221a. In this way, fluid tracking through the absorbent layer 1221, for example, up to the area of the absorbent layer underlying the port or fluidic connector 1211, may track through the uncompressed portions 1221b, but may be impeded, or otherwise experience reduced flow relative to a substantially similar wound dressing as described herein that does not include an absorbent layer comprising one or more compressed portions 1221a.

In some embodiments an absorbent layer 1221 may comprise one, two, three, four, five, six, or more compressed portions 1221a. In some embodiments a compressed portion 1221a may comprise an approximately rectangular shape. In some embodiments the compressed portion 1221a may extend across an entire length or width of the absorbent layer to form a 'stripe' or 'bar.' In some embodiments comprising a plurality of compressed portions 1221a, the compressed portions may be arranged parallel to one another to thereby fluidically divide the absorbent layer 1221 into a plurality of uncompressed absorbent portions 1221b. The plurality of compressed portions 1221a may be arranged in regularly repeating pattern or an irregularly repeating pattern. For example, the compressed portions 1221a may be arranged in a striped or grid pattern. Other shapes and arrangements of the one or more compressed portions 1221a are expressly contemplated, including any such arrangement of compressed portions which serves to impede fluid tracking to an area of the absorbent layer at or near the port 1211.

In some embodiments a compressed portion 1221a of the absorbent layer may have a width of from about 1 mm to about 2 cm. In some embodiments a compressed portion 1221a of the absorbent layer may have a width of from about 5 mm to about 1.5 cm. In some embodiments a compressed portion 1221a of the absorbent layer may have a width of about 1 cm. In some embodiments a compressed portion 1221a of the absorbent layer may have a width sufficient to prevent or substantially reduce the flow of fluid from a first uncompressed portion to a second, adjacent uncompressed portion until the first uncompressed portion becomes substantially saturated with fluid, such as wound exudate.

Figure 11A:
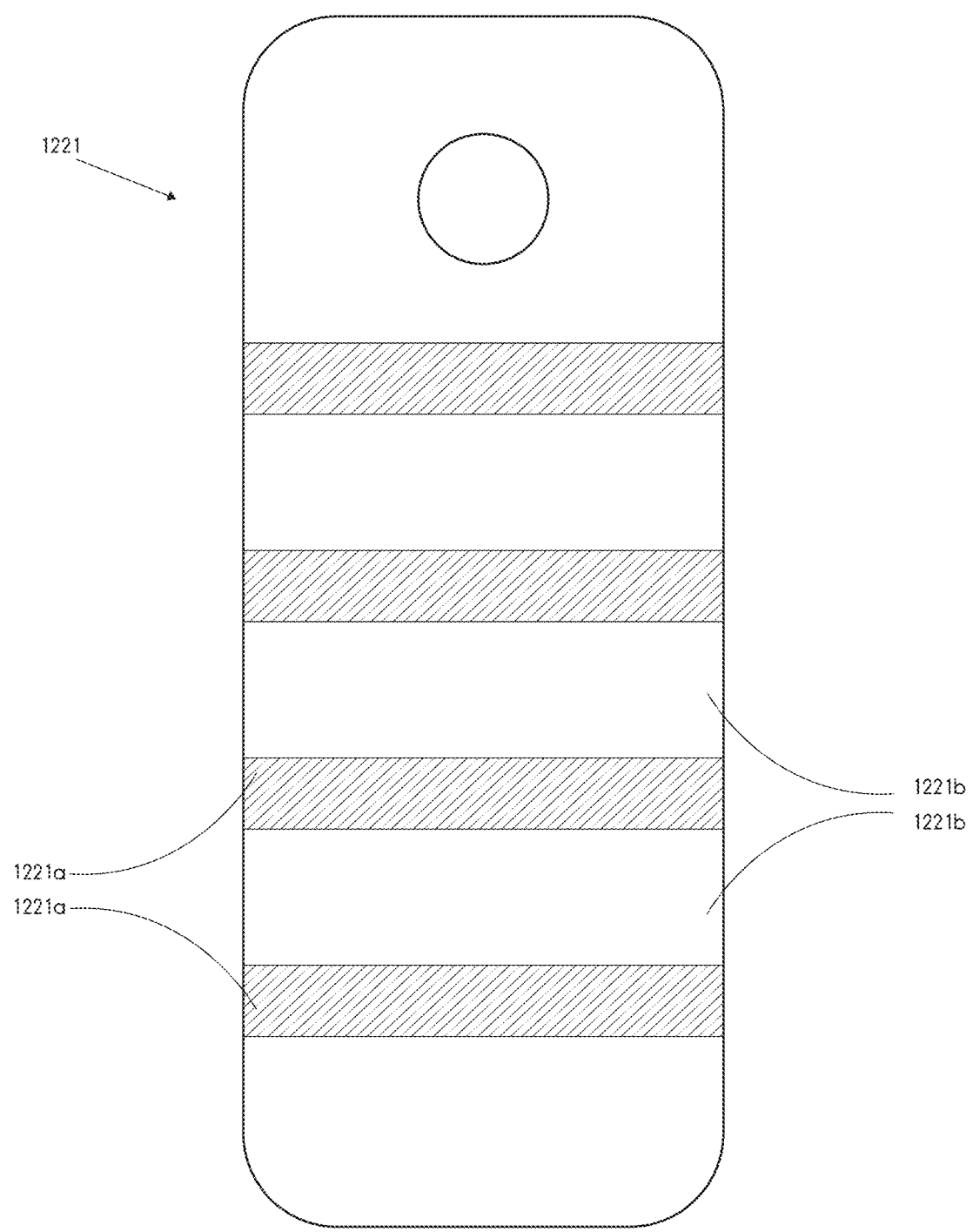
FIG. 11A illustrates an absorbent layer of an embodiment of a wound dressing comprising a compressed portion configured to impede fluid flow between portions of the absorbent layer.
Figure 11B:
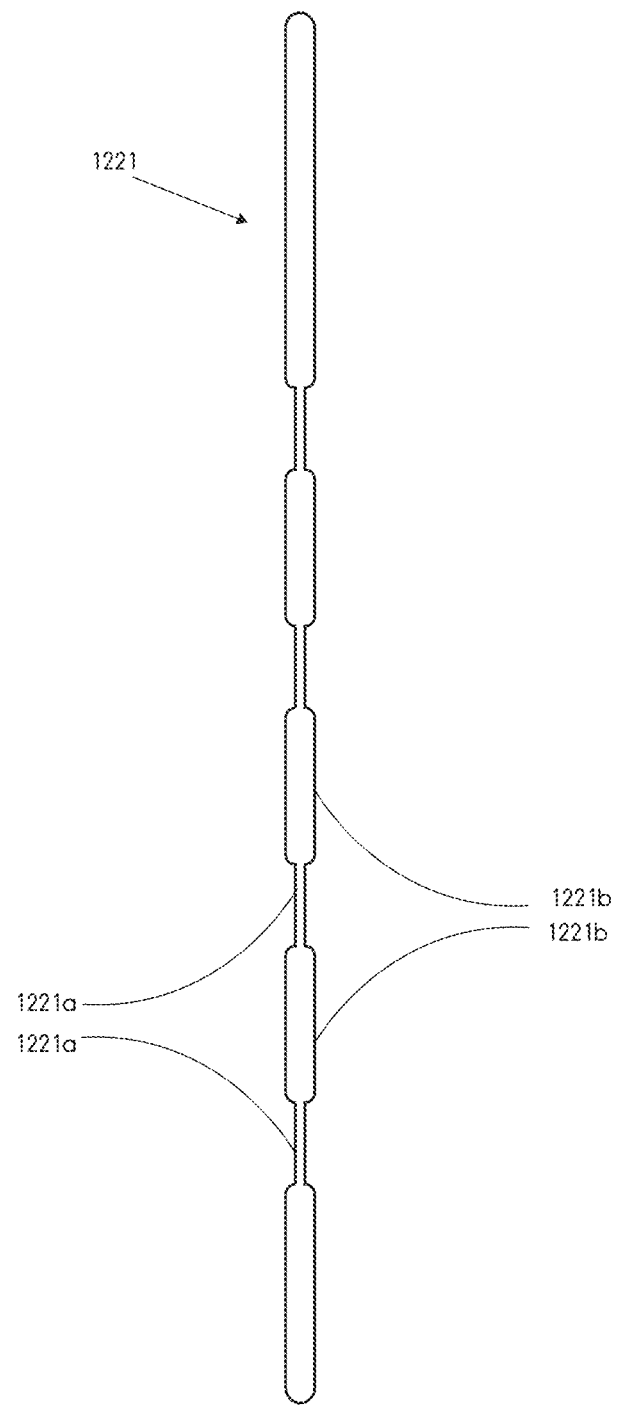
FIG. 11B is a side view of the absorbent layer of FIG. 11A.

As shown in FIGS. 11A-11B, the compressed portions 1221a comprise a rectangular shape and are disposed across the entire width of the absorbent layer 1221. The 4 compressed portions 1221a serve to fluidically divide the absorbent layer 1221 into 5 uncompressed or absorbent portions 1221b, such that the flow of fluid between each of these portions is restricted or impeded relative to an absorbent layer that does not comprise compressed portions. FIG. 11B shows a side view of the absorbent layer 1221. As can be seen, the compressed portions 1221a have a substantially reduced thickness as compared to the uncompressed portions 1221b, which serves to impede fluid flow therethrough.

Figure 11C:
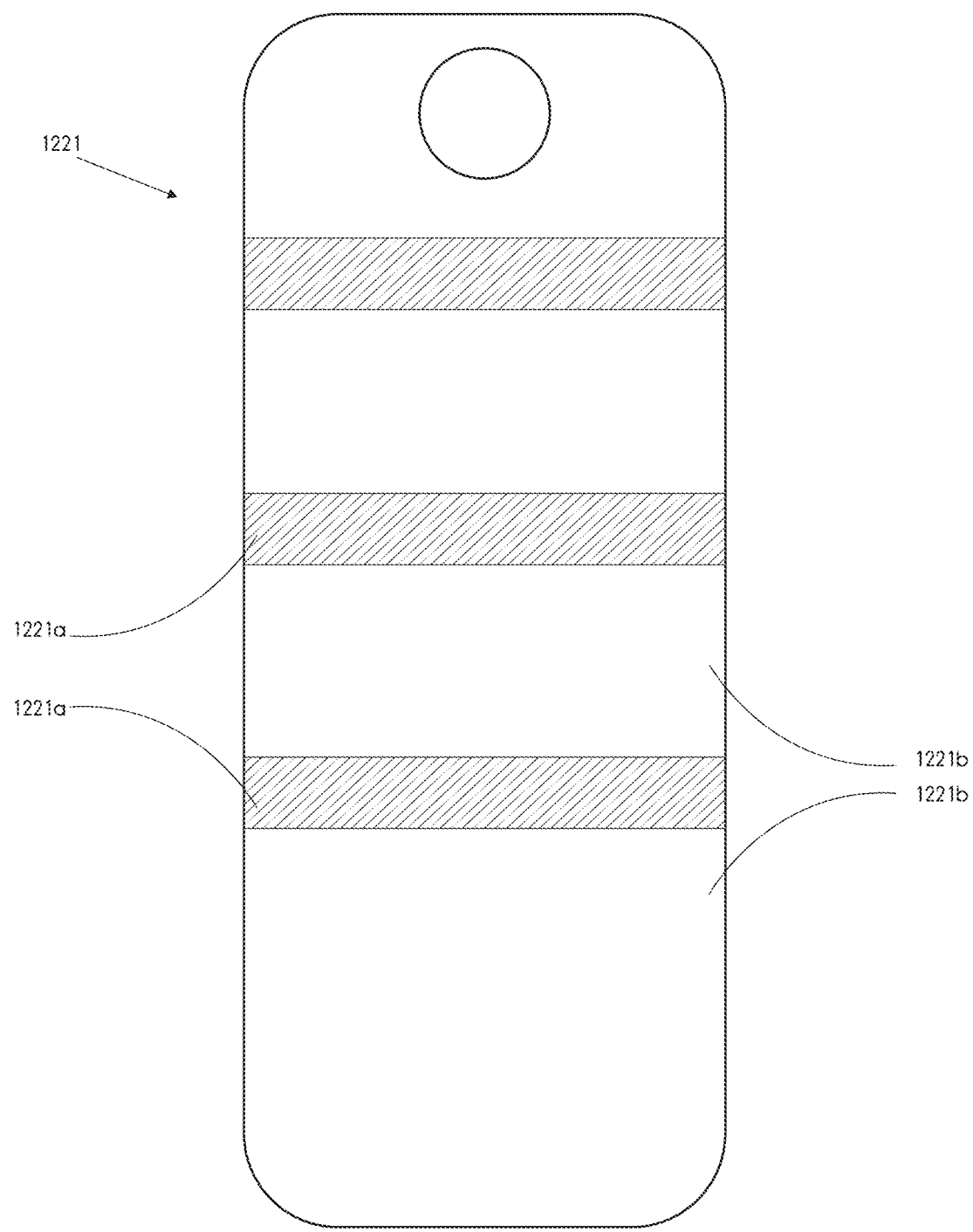
FIG. 11C illustrates an absorbent layer of another embodiment of a wound dressing comprising a compressed portion configured to impede fluid flow between portions of the absorbent layer.

In other embodiments, the size and number of the compressed portions 1221a and the size and number of the uncompressed portions 1221b may vary, provided that the portions extend across substantially the entire length and width of the absorbent layer 1221. For example, more and/or smaller compressed portions 1221a, or fewer and/or larger compressed portions 1221a may comprise the absorbent layer 1221 depending on the expected amount and/or flow rate of exudate from a wound which is to be treated. As can be seen in FIG. 11C, an alternative embodiment may comprise three compressed portions 1221a.

The compressed portions 1221a of the absorbent layer may interrupt fluid flow pathways through the uncompressed portions 1221b of the absorbent layer 1221. For example, in some embodiments described herein, such as wound dressing 100 and 200 which may comprise an absorbent layer 221 that does not comprise compressed portions, a fluid flow pathway may exist from any given portion of the absorbent layer directly to the area of the absorbent layer underlying the port or fluidic connector. These fluid flow pathways can allow for wound exudate that is absorbed by the absorbent layer to track, or flow, through the absorbent layer and preferentially accumulate at or near the port or fluidic connector. However, where the absorbent layer 1221 comprises a plurality of compressed portions 1221a, these fluid flow pathways are interrupted by the compressed portions 1221a between each uncompressed portion 1221b of the absorbent layer.

Figure 12:
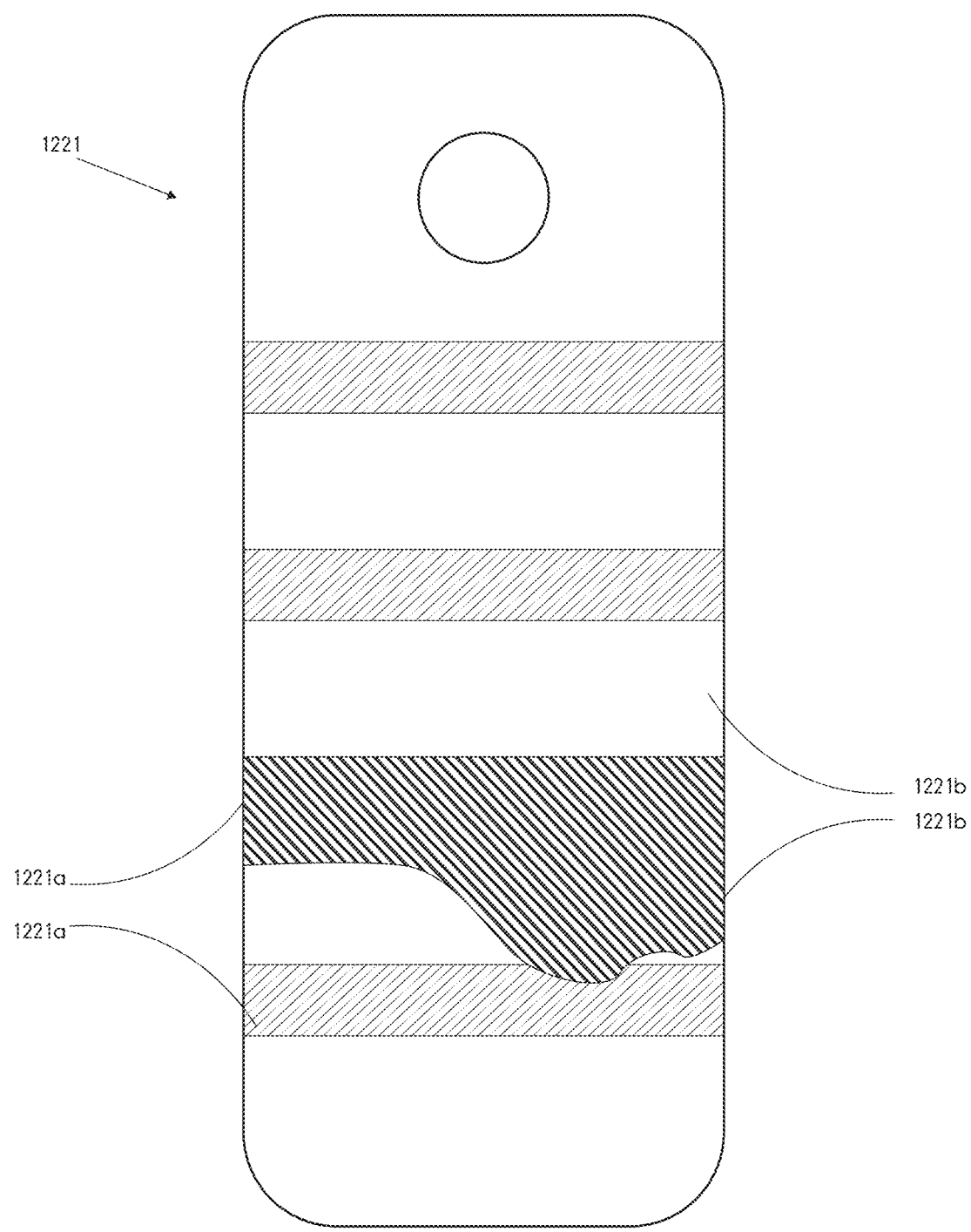
FIG. 12 illustrates the use of an embodiment of a negative pressure wound dressing comprising a compressed portion configured to impede fluid flow between portions of the absorbent layer.

Generally, and as explained in further detail below, fluid will not track from one uncompressed portion 1221b of the absorbent layer to an adjacent portion 1221b unless the initial portion is substantially saturated with exudate. For example, and as can be seen in FIG. 12, the compressed portion 1221a serves to confine fluid, such as wound exudate, in the first uncompressed portion 1221b, thus preventing rapid fluid flow or tracking towards the uncompressed portion 1221b which may underlie the port.

That is, a given portion of the absorbent layer which is absorbing wound exudate may continue to do so, and said exudate may not track or flow therefrom, or may be substantially impeded in tracking or flowing into an adjacent uncompressed portion 1221b of the absorbent layer 1221 until the given portion 1221b is substantially saturated with wound exudate. The adjacent portion 1221b may then absorb fluid at least via the given portion 1221b of the absorbent layer until it has become saturated and the process repeats with an additional uncompressed portion 1221b. Accordingly, uncompressed portions 1221b of the absorbent layer may become substantially saturated before fluid, such as wound exudate, is able to flow or track freely to an adjacent uncompressed portion 1221b. The adjacent portion 1221b may be closer to the port or fluidic connector that is supplying negative pressure to the wound dressing 1200, thus the absorbent layer 1221 may be able to absorb more fluid before the port 1211 becomes blocked or occluded by exudate as compared with a wound dressing that includes an absorbent layer which does not comprise any compressed portions 1221a.

Figure 13:
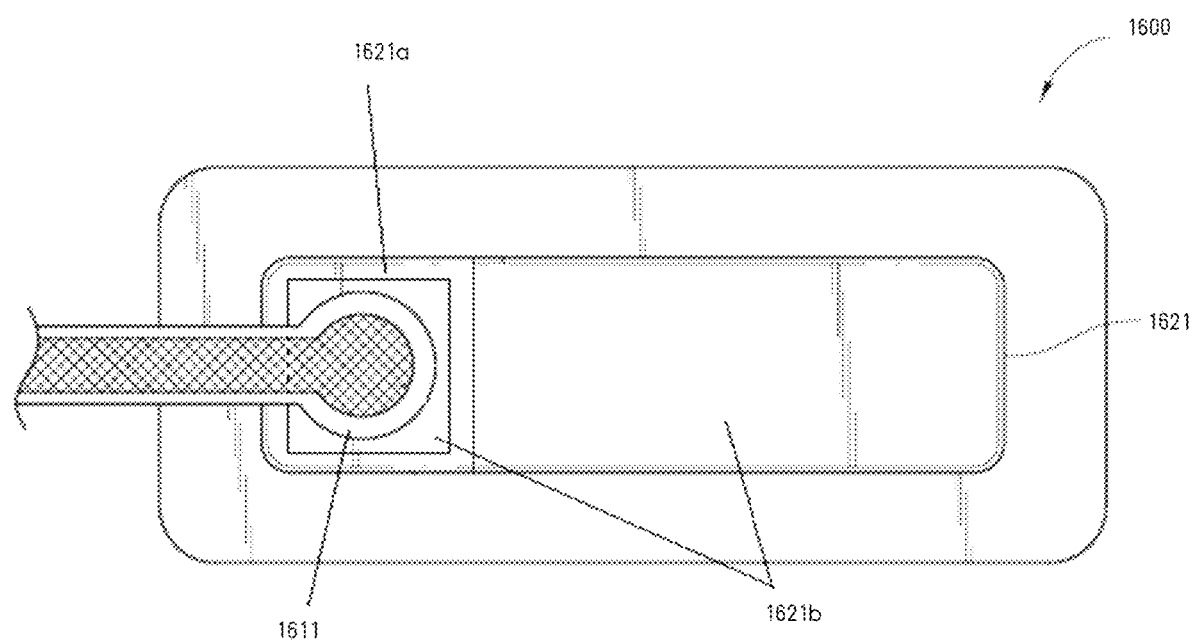
FIG. 13 illustrates a top view of an embodiment of a wound dressing capable of absorbing and storing wound exudate.

FIG. 13 shows a top view of a wound dressing 1600, similar to the dressings described in FIGS. 1A-2B. However, in this embodiment the absorbent layer 1621 comprises a compressed portion 1621a which surrounds an uncompressed portion 1621b that underlies the port or fluidic connector 1611. In some embodiments the compressed portion 1621a may comprise a rectangular shape, as shown in FIG. 13, however in some embodiments the compressed portion 1621a may comprise any other shape which may serve to surround an uncompressed portion 1621b underlying a port of fluidic connector. Similar to the absorbent layer 321, described herein above, the compressed portion 1621a of absorbent layer 1621 serves to fluidically divide the portions 1621b of the absorbent layer adjacent to the compressed portion 1621a. Thus, fluid may be free to flow or track through the first uncompressed portion 1621b of the absorbent layer 1621, but may be substantially impeded from flowing or tracking to the uncompressed portion 1621b underlying the port 1611 until the first uncompressed portion 1621b has been substantially saturated with fluid, such as wound exudate. Accordingly, the compressed portion 1621a may act as a fluidic barrier to prevent or reduce the amount of fluid absorbed at or near the port 1611 during use, thereby extending the useful lifetime of the dressing.

Figure 14A:
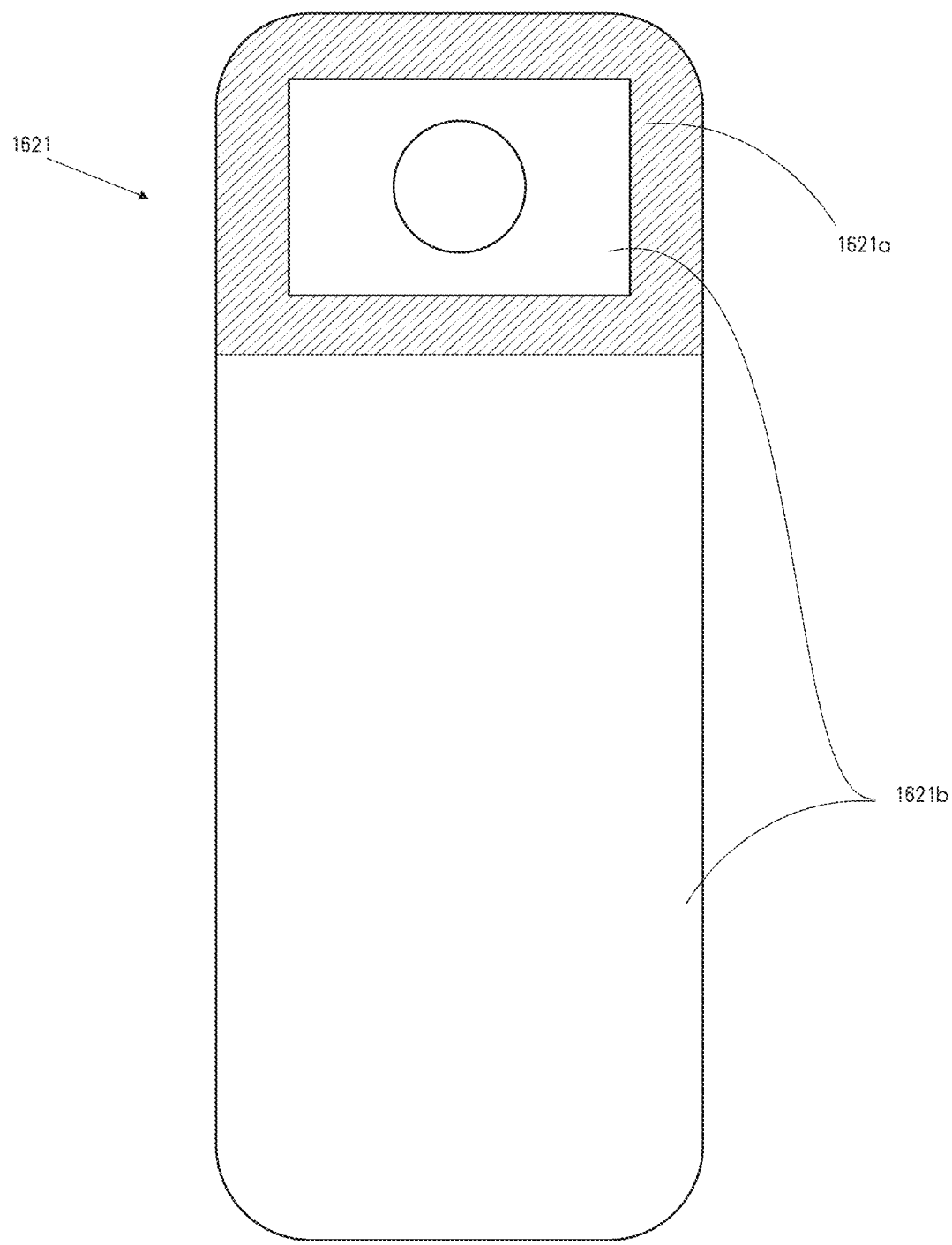
FIG. 14A illustrates an absorbent layer of an embodiment of a wound dressing comprising a compressed portion configured to impede fluid flow between portions of the absorbent layer.
Figure 14B:
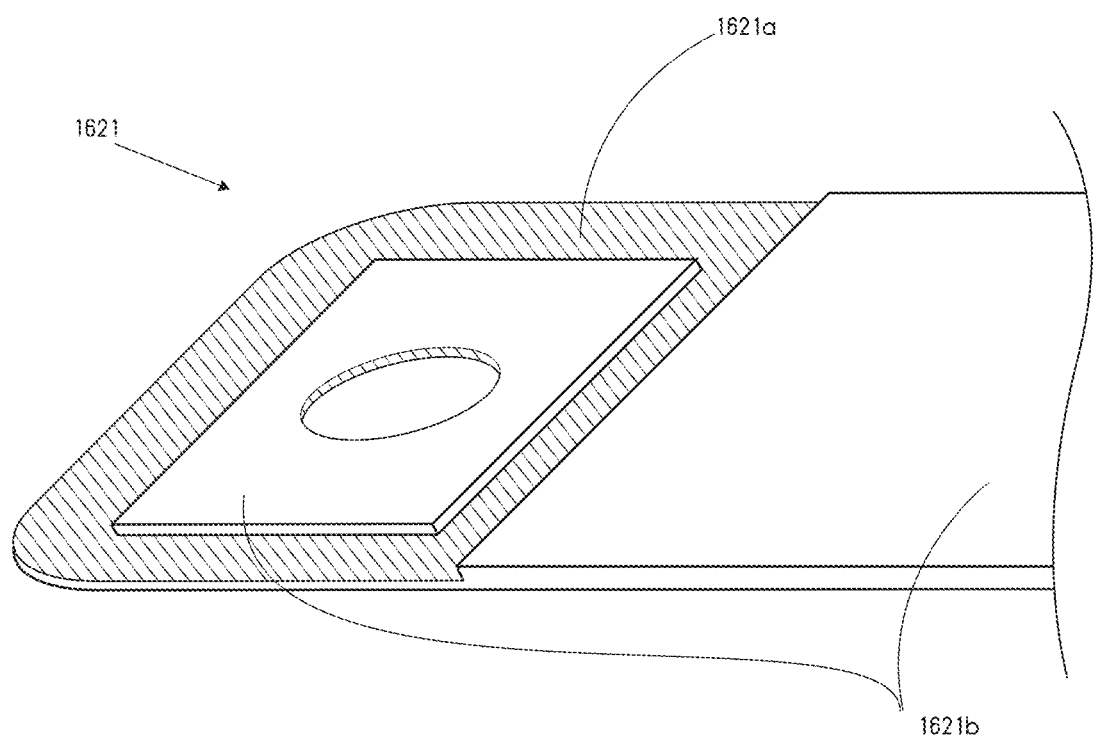
FIG. 14B is a side perspective view of the absorbent layer of FIG. 14A.

FIGS. 14A-14B show the absorbent layer 1621 comprising a compressed portion 1621a surrounding an uncompressed portion 1621b which may underlie a port when included in a wound dressing. In some embodiments such a compressed portion may be formed by exerting heat and/or pressure on desired regions of the absorbent layer 1621, for example via calendering. In some embodiments the compressed portion 1621a may be formed by a single stamp or die having a shape corresponding to the shape of the compressed portion 1621a. However, in some other embodiments the compressed portion 1621a may be formed by a multiple step process, for example by compressing each side portion of a rectangular compressed portion 1621a separately.

In some embodiments where a compressed portion surrounds an uncompressed portion of the absorbent layer, the compressed portion may be understood as a two dimensional shape having a line width of from about 1 mm to about 2 cm. In some embodiments a compressed portion 1621a of the absorbent layer may have a line width of from about 5 mm to about 1.5 cm. In some embodiments a compressed portion 1621a of the absorbent layer may have a line width of about 1 cm. In some embodiments a compressed portion 1621a of the absorbent layer may have a line width sufficient to prevent or substantially reduce the flow of fluid from a first uncompressed portion to a second, adjacent uncompressed portion until the first uncompressed portion becomes substantially saturated with fluid, such as wound exudate.

FIGS. 15A-15D illustrate an embodiment of a wound dressing with an absorbent layer comprising a compressed portion surrounding an uncompressed portion underlying a port or fluidic connector, for example the wound dressing of FIGS. 13-14B.

Figure 15A:
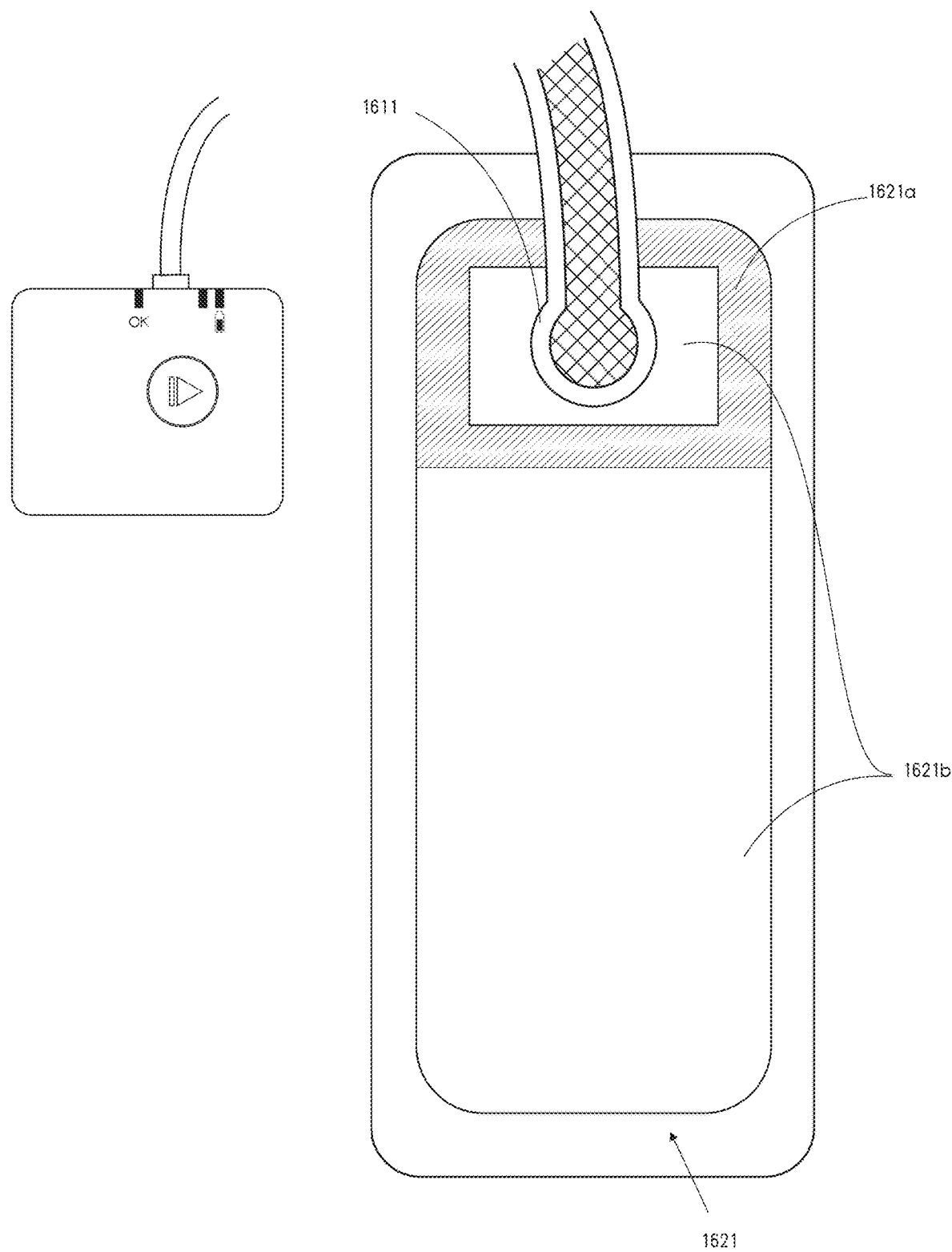
FIGS. 15A-D illustrate the use of an embodiment of a negative pressure wound treatment system employing a flexible fluidic connector and a wound dressing capable of absorbing and storing wound exudate.
Figure 15B:
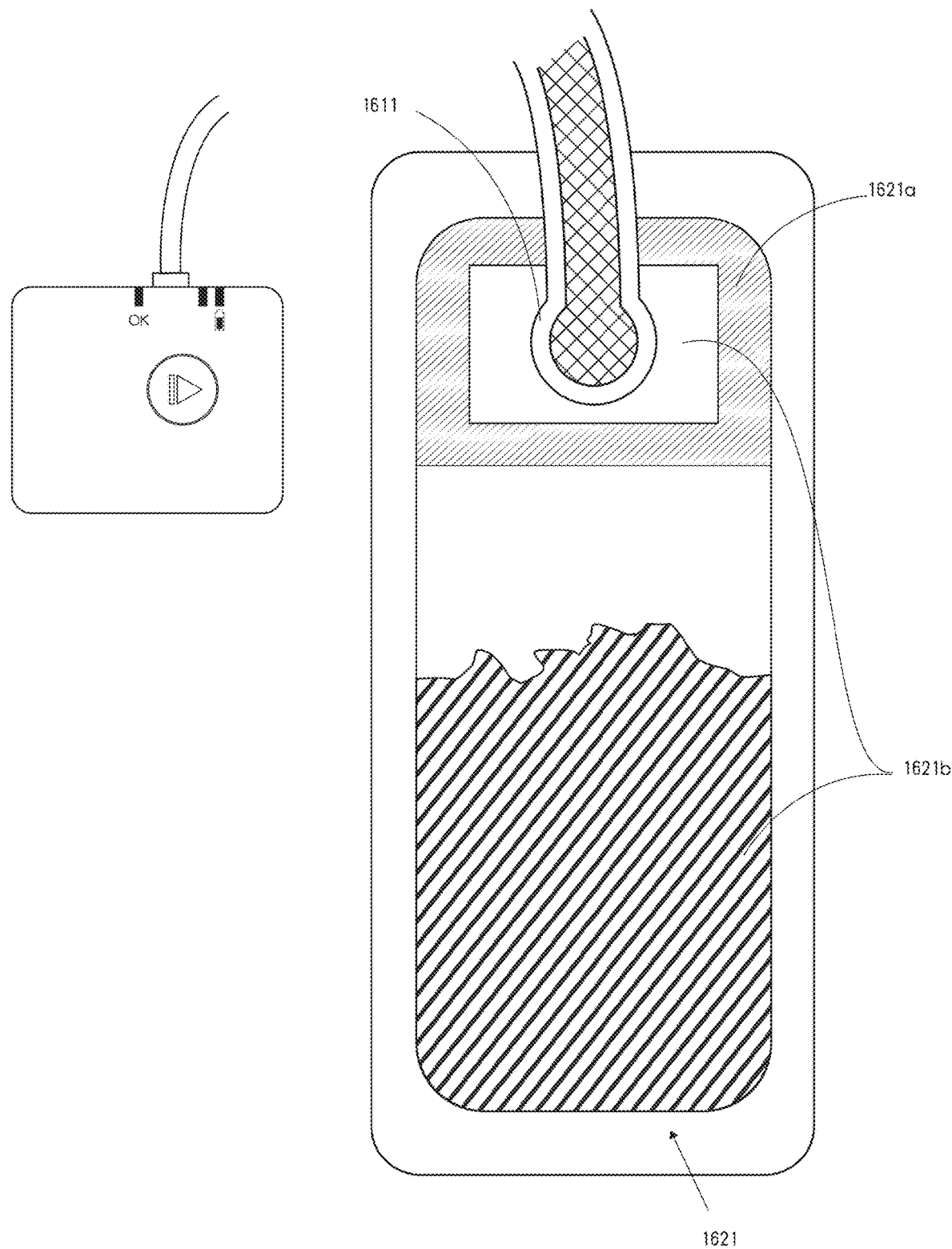
Figure 15C:
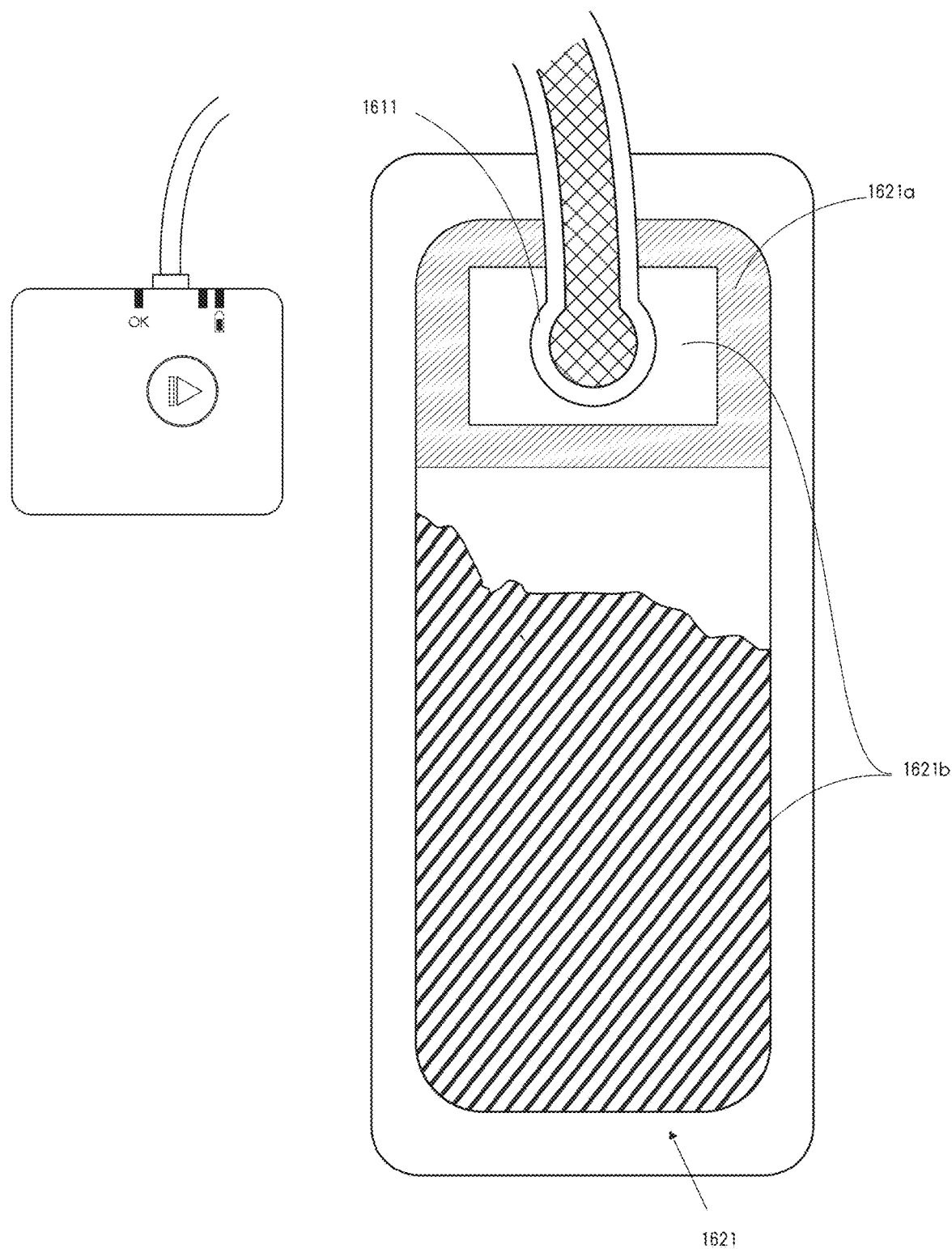
Figure 15D:
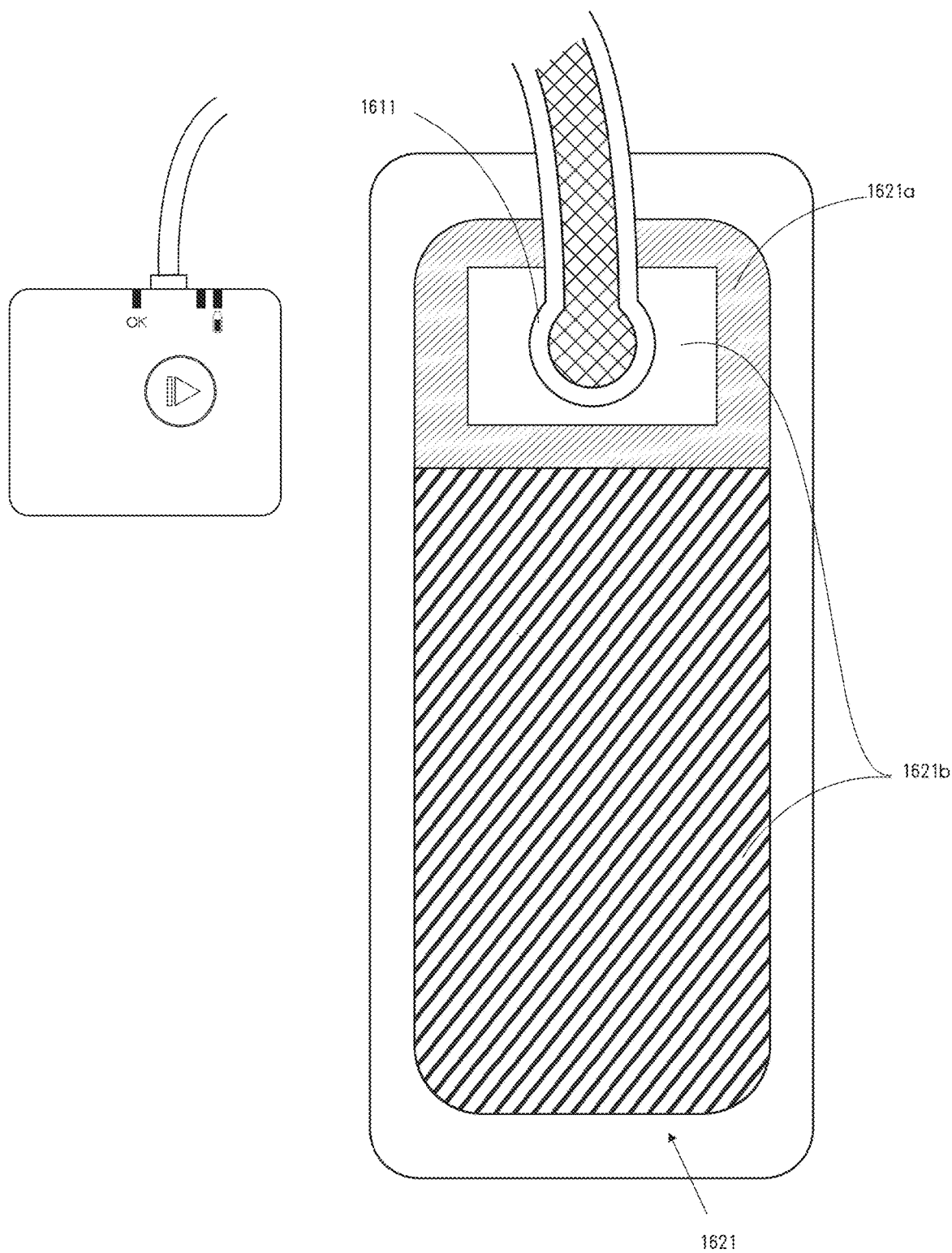

FIG. 15A illustrates an embodiment of a wound dressing comprising an absorbent layer 1621 comprising a compressed portion 1621a surrounding an uncompressed portion 1621b underlying a port or fluidic connector 1611. FIG. 15B illustrates an embodiment of a wound dressing comprising an absorbent layer 1621 comprising a compressed portion 1621a surrounding an uncompressed portion 1621b underlying a port or fluidic connector 1611 as fluid begins to enter the dressing. In some embodiments, when the port is placed at a location away from the wound, as negative pressure is applied, fluid begins to enter the absorbent layer at a location above the wound and furthest from the port as shown in FIG. 15B. As fluid continues to enter the dressing, the dressing will fill up or saturate and fluid will track through the uncompressed portion of the absorbent layer toward the port as illustrated in FIGS. 15C-15D.

In this way, fluid tracking through the absorbent layer 1621, for example to the area of the absorbent layer underlying the port or fluidic connector 1611 may be impeded, or otherwise reduced relative to a substantially similar wound dressing as described herein that does not include an absorbent layer comprising a compressed portion surrounding an uncompressed portion underlying a port or fluidic connector.

When the dressing is positioned so that the port is furthest from the wound, compressed portion or portions of the absorbent layer can control or slow fluid tracking to the port. In this way, the fluidically separate uncompressed portions of the absorbent layer can assist in fluid distribution and handling throughout the absorbent layer. The compressed portions of the absorbent layer can lead to a uniform uptake of fluid in the absorbent layer. The uniform uptake of fluid is accomplished by negating the ability of the fluid to track through the material layer up to the port. The ability to prevent the fluid from tracking to the port can prevent prematurely blocking the port area and stopping therapy.

As described previously, in certain embodiments, such as described above in relation to FIG. 2B, fluid (for example, wound exudate) is handled by the dressing 100 by passing through the perforated wound contact layer 222, into the transmission layer 226, and is then absorbed and retained by the absorbent layer 221. Fluid is then able to evaporate through the breathable backing layer 220. The failure mode of the dressing can be caused by fluid tracking and a premature blocking of the semi-permeable membrane of the fluidic connector by the input liquid. Additionally, the fluid accumulating and protein crusting in the absorbent layer can impede the ability of the dressing to effectively evaporate fluid through the backing layer prior to the failure mode.

It is desirable that the dressing allows NPWT to be delivered without premature blocking of the absorbent layer prior to the dressing becoming full to its liquid capacity. Some embodiments of dressings fail at 3 days, for example due to blockage of the fluid pathway to the fluidic connector. The absorbent layer can preferentially saturate at or near the port prior, thereby leading to blockages. Therefore, as described above, it may be desirable to ensure that fluid is effectively evaporated from the dressing and certain areas of the absorbent layer are preferentially saturated before the areas near the port or fluidic connector, or that the areas of the absorbent layer adjacent the port do not become saturated at all.

Figure 16:
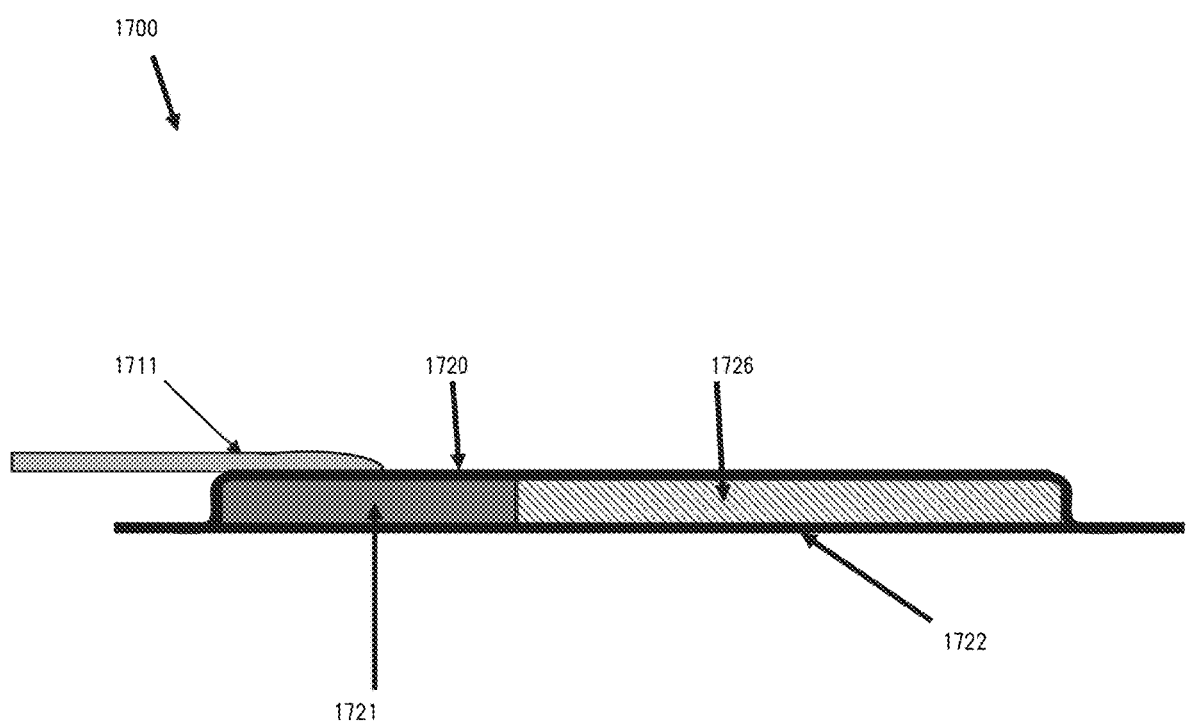
FIG. 16 illustrates a cross section of an embodiment of a wound dressing capable of absorbing and storing wound exudate.

FIG. 16 illustrates an embodiment of a wound dressing 1700, similar to the dressings described in FIGS. 1A-2B. The absorbent layer 1721 and spacer layer 1726 can be similar to the absorbent layer 221 and spacer layer 226 described with reference to FIG. 2B. However, in this embodiment the absorbent layer 1721 and the spacer or transmission layer 1726 as positioned side by side. These side by side absorbent layer 1721 and spacer or transmission layer 1726 may be positioned within the same plane, such as the same horizontal plane when the wound dressing is considered to have a vertical height defined by the thicknesses of its layers and the length and width of the dressing are parallel to the horizontal plane. The absorbent material can be placed at one side of the spacer material (air flow layer or transmission layer) rather than on top of the spacer layer as described in FIG. 2B.

As illustrated in FIG. 16, a cover layer or backing layer 1720 can be positioned over the absorbent layer 1721 and spacer layer 1726. The cover layer 1720 can be similar to the backing layer 220 described with reference to FIGS. 2A-2B. The cover layer 1720 can be sealed to a wound contact layer 1722 at a perimeter of the dressing enclosing the absorbent layer 1721 and spacer layer 1726 between. The wound contact layer 1722 can be similar to the wound contact layer 222 described with reference to FIG. 2B. The cover layer 1720 can have an orifice or aperture above the absorbent layer 1721.

A fluidic connector 1711 can be positioned above the orifice and in fluid communication with a negative pressure source. The fluidic connector 1711 can be similar to the fluidic connector 110 described with reference to FIGS. 2A-2B.

The dressing can include a filter element similar to the filter element described with reference to FIG. 2A-2B. The filter element may also include an odor absorbent material, for example activated charcoal, carbon fiber cloth or Vitec Carbotec-RT Q2003073 foam, or the like. For example, an odor absorbent material may form a layer of the filter element or may be sandwiched between microporous hydrophobic membranes within the filter element. The filter element thus enables gas to be exhausted through the orifice. Liquid, particulates and pathogens however are contained in the dressing. In some embodiments, the dressing can include an odor filter or odor absorbent material including activated carbon, cyclodextrins, and/or zeolites. In some embodiments, the odor filter and/or odor absorbent material can be incorporated into or embedded within any material layer described herein. In other embodiments, the odor filter and/or odor absorbent material can be incorporated into the dressing as a separate layer.

Negative pressure can be applied to the wound site through the fluidic connector 1711 and the wound dressing 1700. As negative pressure is applied, wound exudate can be drawn into the spacer layer 1726 and where possible evaporated from the dressing through the cover layer or backing layer. Any excess fluid not evaporated from the dressing can pass into the absorbent layer 1721. In some embodiments, the absorbent layer 1721 includes super absorbent particles or material. In some embodiments, the absorbent layer 1721 can include a vertical hole (not shown) positioned below the orifice in the backing layer similar to the hole 228 illustrated in FIG. 2B. In other embodiments, the absorbent layer 1721 does not contain a hole in the absorbent material 1721 and the absorbent layer 1721 is positioned below the orifice.

When the absorbent material is positioned on top of the spacer layer, wound fluids can be absorbed by the absorbent material of the dressing and then evaporated out of the cover layer. The positioning of the absorbent layer next to or side by side with the spacer layer can allow negative pressure to be delivered through the dressing and to the wound without premature blocking of the absorbent layer. The spacer layer can be placed over the wound. The backing layer or cover layer can allow liquid from wound exudates to be transferred through the layer and evaporated from an outer surface of the backing layer. The outer surface of the backing layer can be the surface facing away from the wound site or furthest from the wound site when the dressing is placed over the wound. Accordingly, the wound fluid can pass through the wound contact layer into the spacer layer and then evaporate through the cover layer. With this configuration, the wound fluid can be evaporated from the dressing before it can be absorbed by the absorbent material.

In some embodiments, if the fluid volume exceeds the amount that can be evaporated, the excess fluid would be absorbed by the absorbent material. In some embodiments, there is little to no protein crusting or fluid tracking to the port in the absorbent material of the dressing because less fluid enters and is absorbed by the absorbent material.

In some embodiments, the side by side absorbent layer 1721 and spacer layer 1726 can be the only dressing layers between the wound contact layer 1722 and cover layer 1720. In other embodiments, the wound dressing can include additional layers above and/or below the side by side absorbent layer 1721 and spacer layer 1726. For example, the wound dressing can include multiple absorbent layers positioned above and/or below the side by side absorbent layer 1721 and spacer layer 1726. In some embodiments, the wound dressing can include one or more spacer layers positioned above and/or below the side by side absorbent layer 1721 and spacer layer 1726.

Figure 17A:
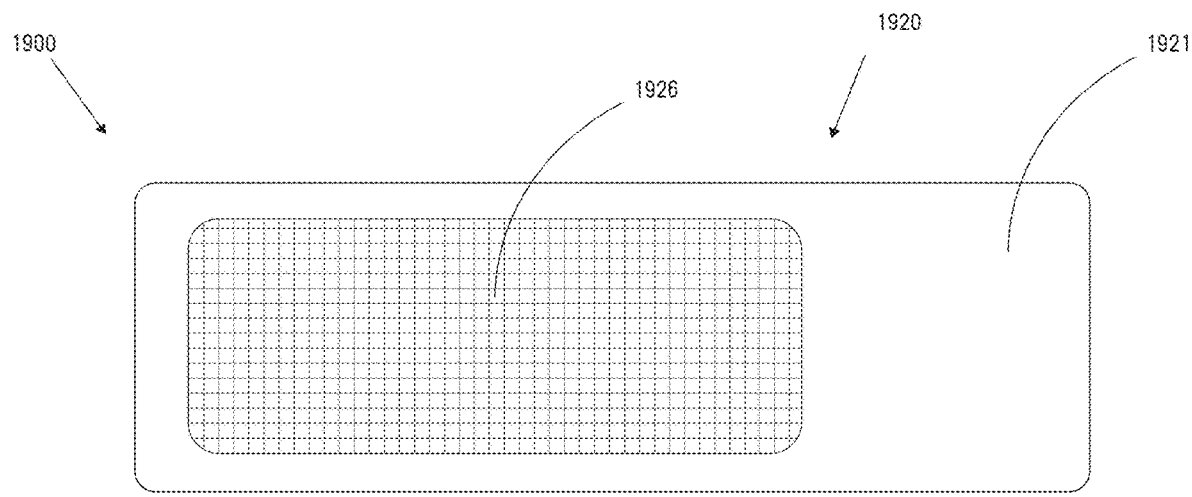
FIGS. 17A-17B illustrate an embodiment of a wound dressing comprising side by side absorbent and spacer materials with the absorbent material around the outside of the spacer layer.
Figure 17B:
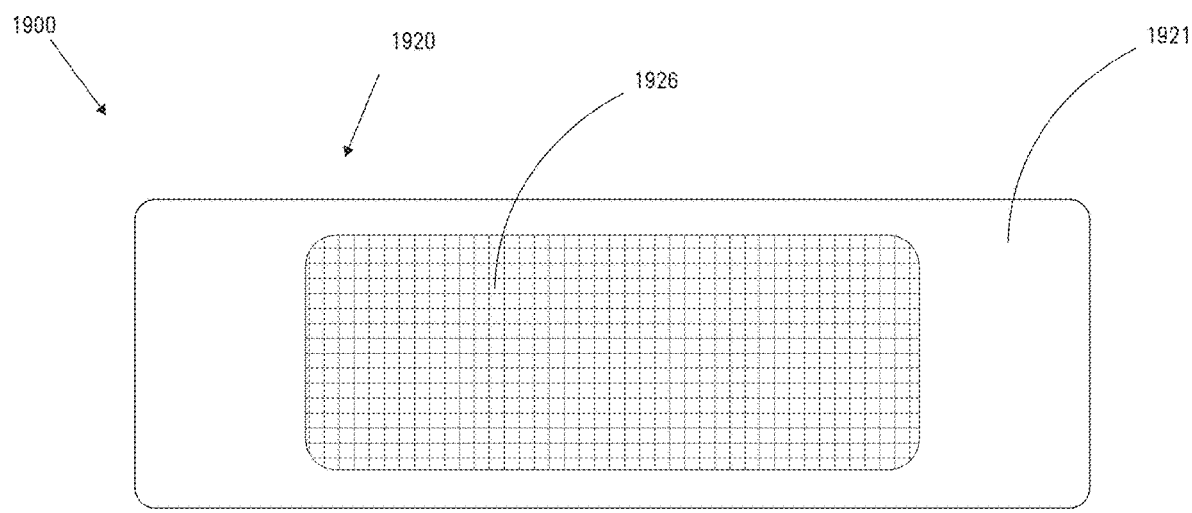

FIGS. 17A-17B illustrate an embodiment of a wound dressing comprising side by side absorbent and spacer materials with the absorbent around the outside of the spacer layer. The absorbent layer 1921 and spacer layer 1926 can be located side by side or within the same horizontal plane. As shown in FIGS. 17A-17B, the absorbent layer 1921 can be located around the outer perimeter of the spacer layer 1926. In some embodiments, the spacer layer 1926 can be positioned surrounded by the absorbent material and more to one side of the wound dressing as shown in FIG. 17A. In other embodiments, the spacer layer 1926 can be positioned in the center of the dressing with the absorbent layer 1921 located around the outer perimeter of the spacer layer 1926 as illustrated in FIG. 17B. In some embodiments, as illustrated, the absorbent layer may comprise a single orifice to receive the spacer layer. In other embodiments, multiple orifices may be provided. The absorbent layer and the spacer layer may have similar shapes or shapes that differ from each other. As illustrated, the absorbent layer and the spacer layer may both have a rectangular shape, optionally with rounded corners.

When the absorbent layer 1921 is located around the outer perimeter of the spacer layer 1926, the design can also provide leak protection to the dressing. In some embodiments, the absorbent layer can provide leak protection by absorbing excess fluid at the edge of the dressing rather than the fluid leaking out of an edge of the dressing. In some embodiments, the absorbent layer 1921 includes super absorbent particles or material. In some embodiments, the super absorbent particles can assist in providing leak protection for the dressing.

A cover layer 1920 can be positioned over the absorbent layer 1921 and spacer layer 1926 as shown in FIG. 17A-17B. The cover layer 1920 can be sealed to a wound contact layer (not shown) at a perimeter of the dressing enclosing the absorbent layer 1921 and spacer layer 1926 between. The cover layer 1920 can have an orifice or aperture (not shown). The orifice or aperture (not shown) can be positioned above the absorbent layer 1921. In some embodiments, the absorbent layer 1921 can include a vertical hole (not shown) positioned below the orifice in the backing layer similar to the hole 228 illustrated in FIG. 2B. A fluidic connector can be applied over the orifice in the cover layer over the absorbent layer to apply negative pressure to the wound dressing. The vertical hole can prevent premature blockage of the fluidic connector when fluid is absorbed by the absorbent layer. In other embodiments, the absorbent layer 1921 does not contain the vertical hole below the orifice in the backing layer. In some embodiments, the cover layer 1920 can have an orifice or aperture (not shown) positioned above the spacer layer 1926 and the fluidic connector can be applied over the orifice above the spacer layer 1926.

When the dressing is positioned so that the port is furthest from the wound, the absorbent layer is positioned further from the wound and the configuration of the spacer layer next to the absorbent layer can control or slow fluid tracking to the port. The spacer layer can be placed over the wound and wound fluid can pass through the wound contact layer into the spacer layer to be evaporated from the dressing before contacting the absorbent material. In this way, the side by side spacer layer and absorbent layer can allow for more fluid to be evaporated from the dressing prior to failure of the dressing than is seen with the stacked configuration described with reference to FIG. 2B. The ability to evaporate fluid directly from the spacer layer before it reaches the absorbent layer can prevent the fluid from tracking to the port and can prevent prematurely blocking the port area and stopping therapy.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, and/or adjacent to the backing layer. In some embodiments, the wound dressing can include a second cover layer and/or a second filter layer for positioning over the layers of the wound dressing and any of the integrated components. The second cover layer can be the upper most layer of the dressing or can be a separate envelope that encloses the integrated components of the topical negative pressure system.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus comprising:
   a wound dressing configured to be positioned over a wound site, the wound dressing comprising:
   a material layer comprising a plurality of tessellating segments, wherein each segment of the plurality of tessellating segments is positioned in the same plane and is at least partially physically separated from adjacent segments by cuts in the material layer along every side of each segment that faces a side of an adjacent segment, and wherein every side of each segment that faces the side of an adjacent segment is configured to contact the side of the adjacent segment prior to flexing of the material layer and is configured to separate away from the side of the adjacent segment during flexing of the material layer;
   a backing layer over the material layer and comprising at least one orifice;
   a wound contact layer beneath the material layer and sealed to the backing layer; and a fluidic connector positioned over the at least one orifice configured to provide negative pressure through the wound dressing to the wound site.

2. The wound treatment apparatus of claim 1, wherein the backing layer is configured to extend at least partially into a space separating a segment of the plurality of tessellating segments from an adjacent segment during flexing of the material layer.

3. The wound treatment apparatus of claim 2, wherein the backing layer comprises folds configured to extend into the space.

4. The wound treatment apparatus of claim 1, further comprising a first transmission layer beneath the material layer.

5. The wound treatment apparatus of claim 1, wherein the plurality of tessellating segments comprise a first segment and second segment, wherein the first segment is larger than the second segment.

6. The wound treatment apparatus of claim 1, wherein the plurality of tessellating segments each have a shape selected from the group consisting of a square, rectangle, circle, pentagon, hexagon, octagon, and triangle.

7. The wound treatment apparatus of claim 1, wherein the plurality of tessellating segments have a rectangular shape.

8. The wound treatment apparatus of claim 1, wherein the material layer comprises the plurality of tessellating segments all of which have the same shape and size.

9. The wound treatment apparatus of claim 1, wherein the material layer comprises the plurality of tessellating segments arranged in a regularly repeating grid pattern.

10. The wound treatment apparatus of claim 1, further comprising a source of negative pressure configured to be in fluid communication with the wound site through the wound dressing.

11. The wound treatment apparatus of claim 1, further comprising a second transmission layer above the material layer.

12. The wound treatment apparatus of claim 1, wherein the fluidic connector comprises a filter.

13. The wound treatment apparatus of claim 1, wherein the material layer comprises an absorbent layer.

14. The wound treatment apparatus of claim 13, wherein the absorbent layer comprises foam.

15. The wound treatment apparatus of claim 1, wherein the plurality of tessellating segments comprise a first segment and second segment of the material layer, wherein the material layer comprises a connecting material connecting the first and second segments.

* * * * *